United States Patent
Bian et al.

(10) Patent No.: US 11,020,425 B2
(45) Date of Patent: Jun. 1, 2021

(54) INJECTABLE HYDROGELS THAT PROMOTE MINERALIZATION AND AFFORD SUSTAINED RELEASE OF BIOACTIVE IONS

(71) Applicant: The Chinese University of Hong Kong, Hong Kong (CN)

(72) Inventors: Liming Bian, Hong Kong (CN); Kunyu Zhang, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 337 days.

(21) Appl. No.: 15/847,174

(22) Filed: Dec. 19, 2017

(65) Prior Publication Data

US 2018/0169141 A1 Jun. 21, 2018

Related U.S. Application Data

(60) Provisional application No. 62/436,035, filed on Dec. 19, 2016.

(51) Int. Cl.
*A61K 31/80* (2006.01)
*A61K 9/00* (2006.01)
(Continued)

(52) U.S. Cl.
CPC .......... *A61K 31/80* (2013.01); *A61K 9/0024* (2013.01); *A61K 9/06* (2013.01); *A61K 9/143* (2013.01);
(Continued)

(58) Field of Classification Search
None
See application file for complete search history.

(56) References Cited

U.S. PATENT DOCUMENTS 6,372,257 B1 * 4/2002 Marchosky ............. A61L 27/26
424/421
2004/0253181 A1 * 12/2004 Port ................... A61K 49/1842
424/9.3
(Continued)

FOREIGN PATENT DOCUMENTS

EP          1160286 A1 * 12/2001  ............. A61L 15/60
WO     2005107714 A2    11/2005
(Continued)

OTHER PUBLICATIONS

Wang et al. "The first pamidronate containing polymer and copolymer", Chem. Commun., May 2006, pp. 2795-2797. (Year: 2006).*
(Continued)

*Primary Examiner* — Katherine Peebles
*Assistant Examiner* — Casey S Hagopian
(74) *Attorney, Agent, or Firm* — Kilpatrick Townsend & Stockton LLP

(57) ABSTRACT

The present invention provides a hybrid hydrogel stabilized by multivalent cross-linking domains. The hydrogel combines inorganic nanoparticles along with an organic polymer network. The resulting material has reinforced mechanical properties and significant mineralization, and affords sustained long-term release of ions. Furthermore, ions released from the hydrogel can enhance cell spreading and promote the osteogenic differentiation of implanted cells. These promising results indicates that the provided compositions and methods are particularly appealing for bone regenerative applications.

13 Claims, 21 Drawing Sheets

(51) Int. Cl.
*A61L 27/52* (2006.01)
*A61L 27/16* (2006.01)
*A61L 27/54* (2006.01)
*A61L 27/38* (2006.01)
*A61K 9/06* (2006.01)
*A61K 47/02* (2006.01)
*A61K 9/14* (2006.01)
*A61K 47/32* (2006.01)

(52) U.S. Cl.
CPC .............. *A61K 47/02* (2013.01); *A61K 47/32* (2013.01); *A61L 27/16* (2013.01); *A61L 27/3834* (2013.01); *A61L 27/52* (2013.01); *A61L 27/54* (2013.01); *A61L 2300/102* (2013.01); *A61L 2300/412* (2013.01); *A61L 2300/602* (2013.01); *A61L 2400/06* (2013.01); *A61L 2400/12* (2013.01); *A61L 2430/02* (2013.01)

(56) References Cited

U.S. PATENT DOCUMENTS

| | | | | |
|---|---|---|---|---|
| 2014/0234210 A1* | 8/2014 | Lin | ........................ | A61K 49/00 424/1.21 |
| 2015/0064107 A1* | 3/2015 | Cui | .................... | A61K 49/0093 424/1.29 |
| 2015/0079007 A1* | 3/2015 | Liu | ...................... | A61K 49/186 424/9.322 |
| 2016/0058892 A1* | 3/2016 | Doschak | ................ | A61K 49/10 424/9.32 |

FOREIGN PATENT DOCUMENTS

| | | | | |
|---|---|---|---|---|
| WO | 2006102117 A1 | | 3/2006 | |
| WO | WO-2013009701 A2 * | | 1/2013 | ............... A61K 9/14 |
| WO | 2014168565 A1 | | 10/2014 | |

OTHER PUBLICATIONS

International Search Report in PCT/CN2017/117182, dated Feb. 26, 2018, 5 pages.
Nejadnik et al., "Self-healing hybrid nanocomposites consisting of bisphosphonated hyaluronan and calcium phosphate nanoparticles," Biomaterials 35 (2014) 6918-6929.
Varghese et al., "In Situ Cross-Linkable High Molecular Weight Hyaluronan-Bisphosphonate Conjugate for Localized Delivery and Cell-Specific Targeting: A Hydrogel Linked Prodrug Approach," J. Am. Chem. Soc. 2009, 131, 8781-8783.
Zhang, et al. "Self-assembled injectable nanocomposite hydrogels stabilized by bisphosphonate-magnesium (Mg2+) coordination regulates the differentiation of encapsulated stem cells via dual crosslinking." Advanced Functional Materials 27, No. 34 (2017): 1701642.
Zhang, et al. "Nanocomposite hydrogels stabilized by self-assembled multivalent bisphosphonate-magnesium nanoparticles mediate sustained release of magnesium ion and promote in-situ bone regeneration." Acta biomaterialia 64 (2017): 389-400.

* cited by examiner

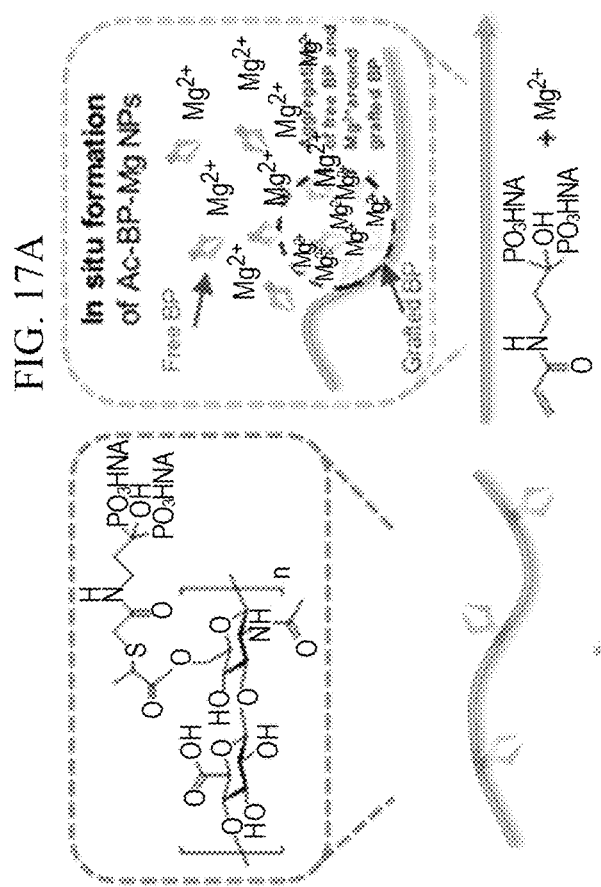
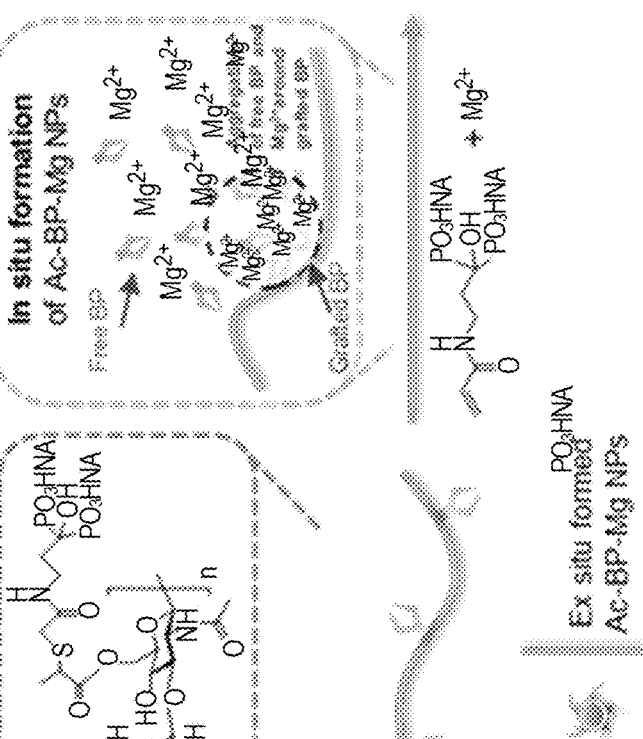
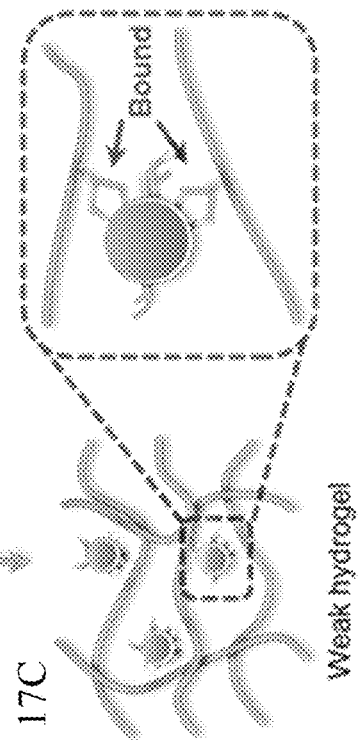
FIG. 17A
FIG. 17B
FIG. 17C
FIG. 17D ial application No. 62/436,035, filed Dec. 19, 2016, the contents of which are hereby incorporated by reference in the entirety for all purposes.

INJECTABLE HYDROGELS THAT PROMOTE MINERALIZATION AND AFFORD SUSTAINED RELEASE OF BIOACTIVE IONS

RELATED APPLICATIONS

This application claims priority to U.S. Provisional Patent Application No. 62/436,035, filed Dec. 19, 2016, the contents of which are hereby incorporated by reference in the entirety for all purposes.

BACKGROUND

Hydrogels are appealing biomaterials for applications in regenerative medicine due to their high water content and tunable physical and biological properties. In recent years, studies have shown that the direct incorporation of inorganic micro/nanoparticles like clay, graphene oxide, and carbon nanotubes further modulates the hydrogel properties, leading to reinforced mechanical behaviors, favorable degradation characteristics, and enhanced bioactivities. However, these approaches usually lead to unstable mixtures of the polymeric and inorganic phases, and hence the inorganic particles tend to separate from the polymeric hydrogel network over an extended period or during the swelling-deswelling process due to the lack of strong interactions between the inorganic particles and the polymer chains.

Bisphosphonates (BP), the analogues of pyrophosphate, have the P—O—P bond replaced by a P—C—P bond which is highly thermostable and resistant to hydrolytic degradation. The two adjacent phosphonic functional groups show excellent efficiency in binding to various metal ions, including $Ca^{2+}$, $Mg^{2+}$, $Fe^{2+}$ and $Cu^{2+}$, thereby affording the potential to interact with various ionic species and nanoparticles. As the potent inhibitors of osteoclasts, bisphosphonates have already been used in clinical conditions characterized by excessive bone resorption, such as osteoporosis, metastatic bone disease, and Paget disease.

Alkaline earth metal ions like $Ca^{2+}$ and $Mg^{2+}$ are critical components of the bone matrix. Calcium intake and deposition is one of the important modifiable environmental factors for the normal development of the skeleton during growth and the maintenance of bone mass. Magnesium ions not only regulate cellular behaviors, such as cell adhesion and differentiation, but also stimulate local bone formation and healing. However, excess Mg ion may lead to bone loss, and a controlled concentration of Mg ion is critical to bone formation. Recent attempts with the use of magnesium and its alloys as orthopedic implant biomaterials have demonstrated promising potentials of magnesium in biomedical applications; yet, the fast degradation of these magnesium metals under physiological conditions leads to the undesirable accumulation of degradation-generated hydrogen gas around the implantation sites. Therefore, for bone repair sites where mechanical support is already secured, the delivery of Mg ion may be a safe and effective way to promote bone regeneration. This demand creates a need for the development of biomaterial vehicles such as hydrogels that are capable of mediating controlled delivery of Mg ion. In addressing this demand, the present inventors by way of their discovery provide surprisingly effective means that meet the need for biomaterials promoting bone repair through the improved release of bioactive ions, as well as other related needs.

SUMMARY OF THE INVENTION

In one aspect, the present invention provides a bisphosphonate-metal nanoparticle, including a bisphosphonate derivative chelated to a metal ion, especially an alkaline earth metal or transition metal ion. In some embodiments, the bisophosphonate derivative is an acrylated bisphosphonate. In some embodiments, the metal is magnesium. In some embodiments, the resulting nanoparticle is a bisphosphonate-magnesium nanoparticle.

In a second aspect, the present invention provides an organic-inorganic hybrid hydrogel, including a plurality of methacrylated polymer chains and a plurality of bisphosphonate-metal nanoparticles covalently linked to the plurality of methacrylated polymer chains. In some embodiments, the polymer is hyaluronic acid. In some embodiments, the bisophosphonate derivative is an acrylated bisphosphonate. In some embodiments, the metal is magnesium.

In a third aspect, the present invention provides an injectable organic-inorganic hybrid hydrogel, including a plurality of bisphosphonated polymer chains and a plurality of bisphosphonate-metal nanoparticles chelated to the plurality of bisphosphonated polymer chains. In some embodiments, the polymer is hyaluronic acid. In some embodiments, the bisophosphonate derivative is an acrylated bisphosphonate. In some embodiments, the metal is magnesium.

In a fourth aspect, the present invention provides a method of generating a bisphosphonate-metal nanoparticle, the method including forming a reaction mixture including a bisphosphonate derivative and a metal halide or nitrate; thereby chelating the bisphosphonate derivative to the metal halide or nitrate and generating the bisphosphonate-metal nanoparticle. In some embodiments, the bisophosphonate derivative is an acrylated bisphosphonate. In some embodiments, the metal is magnesium. In some embodiments, the metal halide or nitrate is magnesium halide.

In a fifth aspect, the present invention provides a method of generating an organic-inorganic hybrid hydrogel, the method including forming a reaction mixture including a methacrylated polymer, a bisphosphonate derivative, a metal halide or nitrate, and an initiator such as a photoinitiator, thereby chelating the bisphosphonate derivative to the metal halide or nitrate to produce bisphosphonate-metal nanoparticles. The method further includes exposing the reaction mixture to ultraviolet (UV) irradiation or other initiators, thereby cross-linking the methacrylated polymer and the bisphosphonate-metal nanoparticles, and generating the organic-inorganic hybrid hydrogel. In some embodiments, the polymer is hyaluronic acid. In some embodiments, the bisophosphonate derivative is an acrylated bisphosphonate. In some embodiments, the metal is magnesium. In some embodiments, the metal halide or nitrate is magnesium halide.

In a sixth aspect, the present invention provides a method of generating an injectable organic-inorganic hybrid hydrogel, the method including forming a reaction mixture comprising bisphosphonated polymer, a phosphonate derivative, and a metal halide or nitrate, thereby chelating the bisphosphonate derivative to the metal halide or nitrate to produce bisphosphonate-metal nanoparticles, chelating the bisphosphonated polymer with the bisphosphonate-metal nanoparticles, and generating the injectable organic-inorganic hybrid hydrogel. In some embodiments, the polymer is hyaluronic acid. In some embodiments, the phosphonate derivative is an acrylated bisphosphonate. In some embodiments, the metal is magnesium. In some embodiments, the metal halide or nitrate is magnesium halide.

In a seventh aspect, the present invention provides a method of filling bone defects, the method including implanting or injecting an organic-inorganic hybrid hydrogel described above and herein into bone defects, and seeding the organic-inorganic hybrid hydrogel with cells.

BRIEF DESCRIPTION OF THE DRAWINGS

FIG. 17A-17D presents a schematic illustration of the fabrication of the HA-BP—Mg self-assembled nanocomposite hydrogel.

(FIG. 18B) A demonstration of the injectability and moldability of the in situ hydrogels. (FIG. 18C) Live/dead staining of the hMSCs encapsulated in the in situ hydrogel after being injected into a star-shaped mold.

FIG. 20A-20D (FIG. 20a, b) Representative oscillatory rheological analysis results and (FIG. 20c, d) average Youngs's modulus of the nanocomposite hydrogels with a series of alkaline earth metal ions ($Mg^{2+}$, $Ca^{2+}$, $Sr^{2+}$, $Ba^{2+}$) and transition metal ions ($Mn^{2+}$, $Fe^{2+}$, $Co^{2+}$, $Ni^{2+}$), respectively.

DEFINITIONS

Figure 1A:
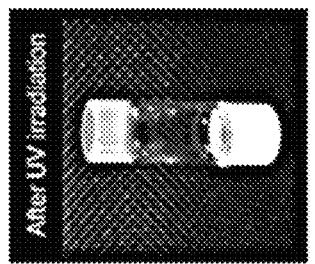
FIGS. 1A-1E presents a schematic illustration of the fabrication of MeHA-BP—Mg hybrid hydrogel.
Figure 1B:
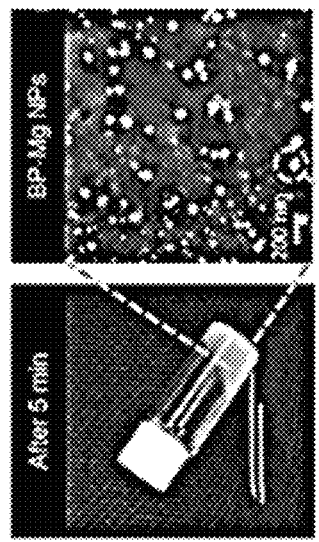
Figure 1C:
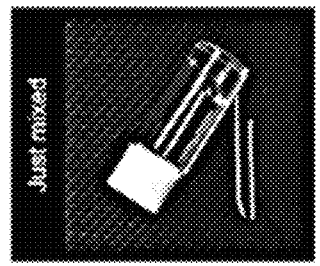
Figure 1E:
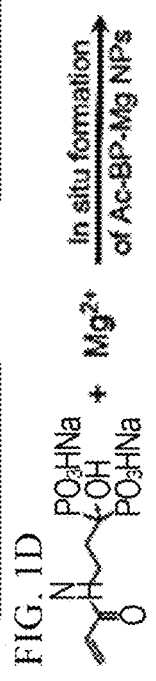
Figure 1E:
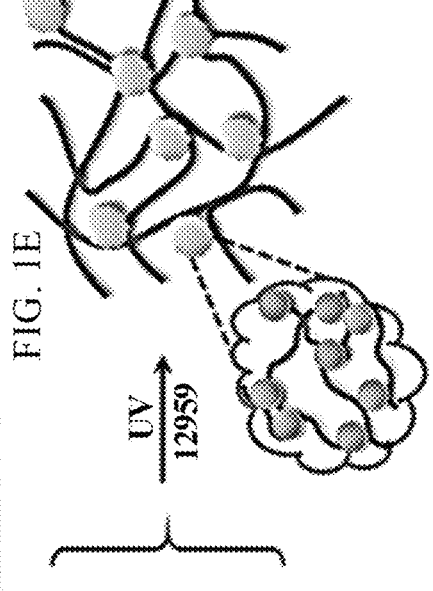
Figure 1E:
Figure 1D:
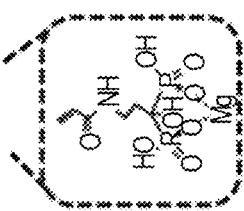
Figure 1D:
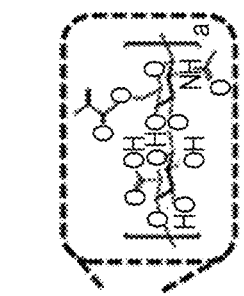

"Nanoparticle" refers to any solid particulate with a size that is in the range of nanometers. For example, a nanoparticle can have a diameter of less than 1 micron (1000 nm), or less than about 100 nm.

"Bisphosphonate-metal nanoparticle" refers to a solid particulate formed by metal ions (especially alkaline earth metal or transition metal ions such as magnesium, calcium, strontium, barium, manganese, iron, cobalt, and nickel) linking bisphosphonates through chelating bonds.

"Hydrogel" refers to a network or scaffolding of natural or synthetic polymer chains that are hydrophilic, sometimes found as a colloidal gel in which water is the dispersion medium. Being polymer networks that have high water-absorbing capacity, hydrogels often closely mimic native extracellular matrices. Hydrogels also tend to possess a degree of flexibility very similar to natural tissues, due to the relatively high water content. In some cases, hydrogels can contain well over 90% water.

"Methacrylate polymer chains" refers to multimeric compounds of a polymer chain, such as the polysaccharide hyaluronic acid, wherein at least a portion of the monomers are derivatized with methacrylate residues. The polymer chains can be of any multimeric length. Other polymers suitable for use in this invention include chitosan, cellulose, and chondroitin sulfate.

"Bead-like cross-linking domain" refers to a microstructure created by the crosslinking of polymer chains and having a generally spherical or ovoid shape. The microstructure can be a localized domain having a relatively high density of cross-linking within a larger network of cross-linked polymers.

"Forming a reaction mixture" refers to the process of bringing into contact at least two distinct species such that they mix together and can react, either modifying one of the initial reactants or forming a third, distinct, species, a product. It should be appreciated, however, the resulting reaction product can be produced directly from a reaction between the added reagents or from an intermediate from one or more of the added reagents which can be produced in the reaction mixture.

"Photoinitiator" refers to a compound that initiates a polymerization process after irradiation. The photoinitiator can generate acid (a photo-acid generator or PAG) or a radical, among other initiating species. The acid, radical, or other species, then initiates a polymerization.

"Biocompatible" refers to a material, composition, device, or method that does not have toxic or injurious effects on biological systems. In some medical applications, a biocompatible material, composition, device, or method does not have toxic or injurious effects on a treated subject.

"Bioactive" refers to a compound having a physiological effect on a biological system or subject as compared to a biological system or subject not exposed to the compound.

"Subject" refers to animals such as mammals, including, but not limited to, primates (e.g., humans), cows, sheep, goats, horses, dogs, cats, rabbits, rats, mice and the like. In certain embodiments, the subject is a human.

DETAILED DESCRIPTION

I. General

The present invention provides compositions and methods for use with injectable biomaterials that promote bone regeneration through the improved release of bioactive ions. In part, the disclosure herein is directed to a novel bisphosphonate-magnesium nanoparticle (BP—Mg NP) cross-linker, which can directly link a polymer network through covalent or chelating bonds. Briefly, upon mixing a methacrylated hyaluronic acid (MeHA), acrylated bisphosphonate (Ac—BP), and magnesium chloride ($MgCl_2$) solutions, BP—Mg nanoparticles bearing the cross-linkable acrylate groups are formed via the efficient chelation between Ac—BP and $Mg^{2+}$. The size of these nanoparticles can be easily tuned by adjusting the concentration of the reactants and mixing time. Subsequent radical polymerization (e.g., initiated by UV radiation) of the free acrylate groups on the surface of the BP—Mg NP crosslinkers and the methacrylate groups on the MeHA polymer chains produces MeHA-BP—Mg organic-inorganic hybrid hydrogels. Alternatively, the magnesium of the BP—Mg crosslinkers can chelate with bisphosphonate groups on bisphosphonated hyaluronic acid to produce injectable organic-inorganic hybrid hydrogels.

Such hydrogels exhibit enhanced mechanical properties when compared with photo-crosslinked pure MeHA hydrogels, and sustain continuous release of Mg ions over a long period. Moreover, the competitive binding to BP by $Ca^{2+}$ present in a surrounding implantation environment can trigger the release of $Mg^{2+}$ from the hydrogels, thereby promoting osteogenesis and bone regeneration at the intended sites. A key advantage of the hydrogel-based Mg ion delivery system is that the hydrogel can be injected to fill up bone defects of irregular geometry via a minimally invasive procedure. Furthermore, the BP-based nanocomposite hydrogel design also allows facile incorporation of other bioactive cationic species such as strontium ions. For at least these reasons, the compositions and methods set forth herein can enable new routes to developing biopolymer-based organic-inorganic hybrid hydrogels with enhanced physical and biological functionalities for regenerative medicine.

II. Nanoparticles

In some embodiments, the present invention provides several bisphosphonate nanoparticles useful for crosslinking to form hydrogels. The nanoparticle can include a biocompatible or bioactive cation. The biocompatible or bioactive cation can be, for example, an alkaline earth metal. The alkaline earth metal can be, for example, magnesium, barium calcium, or strontium. In some embodiments, the nanoparticle is a bisphosphonate-magnesium nanoparticle which includes an acrylated bisphosphonate chelated to magnesium. The bisphosphonate can be any of a class of compounds that share a common P—C—P backbone. The bisphosphonate can be, for example, pamidronate, neridronate, or alendronate.

In some embodiments, the present invention also provides several methods for generating bisphosphonate-magnesium nanoparticles useful for crosslinking to form hydrogels. The methods include forming a reaction mixture that includes acrylated bisphosphonate and magnesium halide. In some embodiments, the magnesium halide is magnesium chloride. The acrylated bisphosphonate chelates to the magnesium and generates the bisphosphonate-magnesium nanoparticle. The simple mixing of acrylated bisphosphonate and magnesium halide solutions leads to the formation of an Ac—BP—Mg nanoparticle suspension within a short period of time due to this rapid chelation between bisphosphonate and $Mg^{2+}$.

The concentration of acrylated bisphosphonate in the reaction mixture to generate bisphosphonate-magnesium nanoparticles can be within the range between 10 mM and 2 M. The concentration of acrylated bisphosphonate can be within the range between 20 mM and 50 mM, between 50 mM and 500 mM, or between 500 mM and 2 M. The concentration of acrylated bisphosphonate can be within the range between 50 mM and 150 mM, between 150 mM and 250 mM, between 250 mM and 350 mM, between 350 mM and 450 mM, or between 450 mM and 550 mM. In some embodiments, the concentration of acrylated bisphosphonate in the reaction mixture is within the range between 10 mM and 1 M.

The concentration of magnesium halide in the reaction mixture to generate bisphosphonate-magnesium nanoparticles can be within the range between 10 mM and 2 M. The concentration of magnesium halide can be within the range between 1 mM and 10 mM, between 10 mM and 250 mM, or between 250 mM and 1 M. The concentration of magnesium halide can be within the range between 10 mM and 50 mM, between 50 mM and 100 mM, between 100 mM and 150 mM, between 150 mM and 200 mM, or between 200 mM and 250 mM. In some embodiments, the concentration of magnesium halide in the reaction mixture is within the range between 10 mM and 1 M.

The bisphosphonate-magnesium nanoparticles can be generated less than 30 seconds, less than 2 minutes, less than 3 minutes, less than 4 minutes, less than 5 minutes, less than 6 minutes, less than 7 minutes less than 8 minutes, less than 9 minutes, less than 10 minutes, less than 20 minutes, less than 30 minutes, less than 40 minutes, less than 50 minutes, or less than 1 hour after forming the reaction mixture. In some embodiments, the bisphosphonate-magnesium nanoparticles are generated less than 5 minutes subsequent to the forming of the reaction mixture.

In some embodiments, the concentration of acrylated bisphosphonate in the reaction mixture is within the range from 10 mM to 1 M, the concentration of magnesium halide in the reaction mixture is within the range from 10 mM to 1 M, and the bisphosphonate-magnesium nanoparticle is generated less than 5 minutes subsequent to the forming of the reaction mixture.

Although the methods described above include magnesium, it should be appreciated that the present invention is not limited to this metal. The bisphosphonate nanoparticles and the methods for their production can include one or more of any bioactive or biocompatible metals. In some embodiments, the metal is an alkaline earth metal or a transition metal. The alkaline earth metal can be, for example, strontium, calcium, magnesium, or barium, and the transition metal can be, for example, manganese, iron, cobalt, or nickel. Similarly, the magnesium halide of the method for generating nanoparticles can be substituted by strontium halide, calcium halide, or the like. The strontium, calcium, or other metal would then participate in the chelation of the method, thereby generating the bisphosphonate nanoparticle. In some embodiments, the metal is selected from among bioactive metallic ions that promote tissue regeneration.

III. Hydrogels

In some embodiments, the present invention provides several organic-inorganic hybrid hydrogels. The hydrogels can include one or more biocompatible or bioactive cations. The biocompatible or bioactive cations can be, for example, alkaline earth metals. The alkaline earth metals can be, for example, one or more of magnesium, calcium, barium, or strontium. In some embodiments, the organic-inorganic hybrid hydrogel includes a plurality of methacrylated hyaluronic acid polymer chains, and a plurality of bisphosphonate-magnesium nanoparticles covalently linked to the plurality of methacrylated hyaluronic acid polymer chains.

The hydrogels can be formed through the ultraviolet-initiated polymerization of the free acrylate groups on the surface of the Ac—BP—Mg nanoparticles described above, and the methacrylate groups on the methacrylated hyaluronic acid polymer chains. This polymerization produces the photo-crosslinked MeHA-BP—Mg hybrid hydrogels. Within the hydrogels, the Ac—BP—Mg NPs can be randomly crosslinked to each other or to free polymer chains, forming bead-like, micrometer-sized micro-domains or microstructures. These micro-domains formed by the clustering of the Ac—BP—Mg NPs act as multivalent cross-linked structures that help stabilize the hydrogel network. The hydrogel can be formed from nanoparticles that have been previously generated and isolated prior to a subsequent cross-linking or polymerization, or the hydrogel can be formed concurrently with the generation of the nanoparticles in a one-pot process.

At least a portion of the covalent linkages between the methacrylated hyaluronic acid polymer chains and the bisphosphonate-magnesium nanoparticles of the organic-inorganic hybrid hydrogel can form bead-like microstructures within the hydrogel. These microstructures typically have a size that is larger than that of the nanoparticles themselves, or physical aggregates of the nanoparticles. The average diameter of the bead-like microstructures within the hydrogel can be within the range from 300 nm to 10 µm. The average diameter can be within the range from 300 nm to 1 µm, from 1 µm to 3 µm, or from 3 µm to 10 µm. The average diameter can be within the range from 1 µm to 1.4 µm, from 1.4 µm to 1.8 µm, from 1.8 µm to 2.2 µm, from 2.2 µm to 2.6 µm, or from 2.6 µm to 3 µm. In some embodiments, the average diameter of the bead-like microstructures within the hydrogel is within the range from 500 µm to 5 µm.

In some embodiments, the present invention also provides several methods for generating organic-inorganic hybrid hydrogels. The methods include forming a reaction mixture comprising methacrylated hyaluronic acid, acrylated bisphosphonate, magnesium halide, and a photoinitiator. The reaction mixture is then exposed to ultraviolet (UV) irradiation, thereby generating the organic-inorganic hybrid hydrogel. In some embodiments, the magnesium halide is magnesium chloride.

The concentration of methacrylated hyaluronic acid in the reaction mixture to generate organic-inorganic hybrid hydrogels can be within the range between 0.2% w/v and 20% w/v. The concentration of methacrylated hyaluronic acid can be within the range between 0.2% w/v and 0.5% w/v, between 0.5% w/v and 5% w/v, or between 5% w/v and 20% w/v. The concentration of methacrylated hyaluronic acid can be within the range between 1% w/v and 2% w/v, between 2% w/v and 3% w/v, between 3% w/v and 4% w/v, between 4% w/v and 5% w/v, or between 5% w/v and 6% w/v. In some embodiments, In some embodiments, the concentration of methacrylated hyaluronic acid in the reaction mixture is within the range between 0.5% w/v and 10% w/v.

The concentration of acrylated bisphosphonate in the reaction mixture to generate organic-inorganic hybrid hydrogels can be within the range between 20 mM and 2 M. The concentration of acrylated bisphosphonate can be within the range between 20 mM and 50 mM, between 50 mM and 500 mM, or between 500 mM and 2 M. The concentration of acrylated bisphosphonate can be within the range between 50 mM and 150 mM, between 150 mM and 250 mM, between 250 mM and 350 mM, between 350 mM and 450 mM, or between 450 mM and 550 mM. In some embodiments, the concentration of acrylated bisphosphonate in the reaction mixture is within the range between 10 mM and 1 M.

The concentration of magnesium halide in the reaction mixture to generate organic-inorganic hybrid hydrogels can be within the range between 1 mM and 1 M. The concentration of magnesium halide can be within the range between 1 mM and 10 mM, between 10 mM and 250 mM, or between 250 mM and 1 M. The concentration of magnesium halide can be within the range between 10 mM and 50 mM, between 50 mM and 100 mM, between 100 mM and 150 mM, between 150 mM and 200 mM, or between 200 mM and 250 mM. In some embodiments, the concentration of magnesium halide in the reaction mixture is within the range between 10 mM and 1 M.

The concentration of photoinitiator in the reaction mixture to generate organic-inorganic hybrid hydrogels can be within the range between 0.005% w/v and 0.5% w/v. The concentration of photoinitiator can be within the range between 0.005% w/v and 0.02% w/v, between 0.02% w/v and 0.2% w/v, or between 0.2% w/v and 0.5% w/v. The concentration of photoinitiator can be within the range between 0.05% w/v and 0.08% w/v, between 0.08% w/v and 0.11% w/v, between 0.11% w/v and 0.14% w/v, between 0.14% w/v and 0.17% w/v, or between 0.17% w/v and 0.2% w/v. In some embodiments, the concentration of photoinitiator in the reaction mixture to generate organic-inorganic hybrid hydrogels is within the range between 0.02% w/v and 0.5% w/v.

The UV irradiation to generate the organic-inorganic hybrid hydrogels can have a power within the range between 1 $mW/cm^2$ and 100 $mW/cm^2$. The UV irradiation can have a power within the range between 1 $mW/cm^2$ and 3 $mW/cm^2$, between 3 $mW/cm^2$ and 30 $mW/cm^2$, or between 30 $mW/cm^2$ and 100 $mW/cm^2$. The UV irradiation can have a power within the range between 5 $mW/cm^2$ and 10 $mW/cm^2$, between 10 $mW/cm^2$ and 15 $mW/cm^2$, between 15 $mW/cm^2$ and 20 $mW/cm^2$, between 20 $mW/cm^2$ and 25 $mW/cm^2$, or between 25 $mW/cm^2$ and 30 $mW/cm^2$. In some embodiments, the UV irradiation has a power within the range between 3 mW/cm$^2$ and 30 mW/cm$^2$.

The UV exposure time to generate the organic-inorganic hybrid hydrogels can be less than 2 minutes, less than 4 minutes, less than 6 minutes, less than 8 minutes, less than 10 minutes, less than 20 minutes, less than 30 minutes, less than 40 minutes, less than 50 minutes, or less than 1 hour. In some embodiments, the UV exposure time to generate the organic-inorganic hybrid hydrogels is less than 20 minutes.

In some embodiments, the concentration of the methacrylated hyaluronic acid polymer chain in the reaction mixture is within the range from 0.5% w/v to 10% w/v, the concentration of acrylated bisphosphonate in the reaction mixture is within the range from 10 mM to 1 M, the concentration of magnesium halide in the reaction mixture is within the range from 10 mM to 1 M, the concentration of photoinitiator in the reaction mixture is within the range from 0.02% w/v to 0.5% w/v, the UV irradiation has a power within the range from 3 mW/cm$^2$ to 30 mW/cm$^2$, and the exposing has an exposure time less than 20 minutes.

In some cases, self-assembled BP—Mg nanocomposite hydrogels of this invention can also be generated through an alternative route without hyaluronic acid. In this scenario, the hydrogels can be directly obtained upon the mixing of aqueous solutions of modified BP and the cationic species such as magnesium ions and calcium ions. Subsequent UV-initiated polymerization of the free acrylate groups on the surface of the NPs then stiffen such BP—Mg nanocomposite hydrogels.

In some embodiments, the present invention provides several injectable organic-inorganic hybrid hydrogels. The injectable organic-inorganic hybrid share many similarities with the above organic-inorganic hybrid hydrogels, but do not require the presence of initiators. The hydrogels described above do require initiators for their pre-gel solutions to solidify into hydrogels as it is the initiators that begin the radical polymerization of the methacrylate groups of the methacrylated hyaluronic acid polymer chain, resulting in a gelation. In contrast, the provided injectable hydrogels can solidify automatically, without the presence of an initiator. These injectable hydrogels are instead crosslinked through chelation interactions between bisphosphonate groups of bisphosphonated hyaluronic acid and the nanoparticles. The reference to these hydrogels not requiring initiators as injectable hydrogels is not intended to suggest that those hydrogels that require initiators cannot also be injected into a subject, but is merely to distinguish between the two configurations and formulations.

The injectable inorganic-organic hydrogels can include one or more biocompatible or bioactive cations. The biocompatible or bioactive cations can be, for example, alkaline earth metals. The alkaline earth metals can be, for example, one or more of magnesium, calcium, barium, or strontium. In some embodiments, the injectable organic-inorganic hybrid hydrogel includes a plurality of bisphosphonated hyaluronic acid polymer chains, and a plurality of bisphosphonate-magnesium nanoparticles chelated to the plurality of bisphosphonated hyaluronic acid polymer chains.

The average diameter of the nanoparticles within the hydrogel can be within the range from 10 nm to 100 nm. The average diameter can be within the range from 10 nm to 60 nm, from 20 nm to 70 nm, from 30 nm to 80 nm, from 40 nm to 90 nm, or from 50 nm to 100 nm. The average diameter can be within the range from 20 nm to 32 nm, from 22 nm to 34 nm, from 24 nm to 36 nm, from 26 nm to 38 nm, or from 28 nm to 40 nm. In some embodiments, the average diameter of the nanoparticles within the hydrogel is within the range from 20 nm to 40 nm.

In some embodiments, the present invention also provides several methods for generating injectable organic-inorganic hybrid hydrogels. The methods include forming a reaction mixture including bisphosphonated hyaluronic acid, acrylated bisphosphonate, and magnesium halide. The acrylated bisphosphonate and magnesium halide then self-assemble to produce acrylated bisphosphonate magnesium nanoparticles, and the nanoparticles chelate to the bisphosphonated hyaluronic acid, thereby generating the injectable organic-inorganic hybrid hydrogel. In some embodiments, the magnesium halide is magnesium chloride.

The concentration of bisphosphonated hyaluronic acid in the reaction mixture to generate injectable organic-inorganic hybrid hydrogels can be within the range between 0.2% w/v and 20% w/v. The concentration of bisphosphonated hyaluronic acid can be within the range between 0.2% w/v and 0.5% w/v, between 0.5% w/v and 5% w/v, or between 5% w/v and 20% w/v. The concentration of bisphosphonated hyaluronic acid can be within the range between 1% w/v and 2% w/v, between 2% w/v and 3% w/v, between 3% w/v and 4% w/v, between 4% w/v and 5% w/v, or between 5% w/v and 6% w/v. In some embodiments, the concentration of bisphosphonated hyaluronic acid in the reaction mixture is within the range between 0.5% w/v and 10% w/v.

The concentration of acrylated bisphosphonate in the reaction mixture to generate injectable organic-inorganic hybrid hydrogels can be within the range between 20 mM and 2 M. The concentration of acrylated bisphosphonate can be within the range between 20 mM and 50 mM, between 50 mM and 500 mM, or between 500 mM and 2 M. The concentration of acrylated bisphosphonate can be within the range between 50 mM and 150 mM, between 150 mM and 250 mM, between 250 mM and 350 mM, between 350 mM and 450 mM, or between 450 mM and 550 mM. In some embodiments, the concentration of acrylated bisphosphonate in the reaction mixture is within the range between 10 mM and 1 M.

The concentration of magnesium halide in the reaction mixture to generate injectable organic-inorganic hybrid hydrogels can be within the range between 1 mM and 1 M. The concentration of magnesium halide can be within the range between 1 mM and 10 mM, between 10 mM and 250 mM, or between 250 mM and 1 M. The concentration of magnesium halide can be within the range between 10 mM and 50 mM, between 50 mM and 100 mM, between 100 mM and 150 mM, between 150 mM and 200 mM, or between 200 mM and 250 mM. In some embodiments, the concentration of magnesium halide in the reaction mixture is within the range between 10 mM and 1 M.

In some embodiments, the concentration of the bisphosphonated hyaluronic acid polymer chain in the reaction mixture to generate injectable organic-inorganic hybrid hydrogels is within the range from 0.5% w/v to 10% w/v, the concentration of acrylated bisphosphonate in the reaction mixture is within the range from 10 mM to 1 M, and the concentration of magnesium halide in the reaction mixture is within the range from 10 mM to 1 M.

Although the methods described above include magnesium, it should be appreciated that the present invention is not limited to this metal. The organic-inorganic hybrid hydrogels and the methods for their production can include one or more of any bioactive or biocompatible metals. In some embodiments, the metal is an alkaline earth metal. In some embodiments, the metal is an alkaline earth metal or a transition metal. The alkaline earth metal can be, for example, strontium, calcium, barium, or magnesium, and the transition metal can be, for example, manganese, iron, cobalt, or nickel. Similarly, the magnesium halide of the method for generating organic-inorganic hybrid hydrogels can be substituted by strontium halide, calcium halide, or the like. The strontium, calcium, or other metal would then participate in the chelation of the method, thereby generating the bisphosphonate nanoparticle. In the case of the injectable organic-inorganic hybrid hydrogels, the strontium, calcium, or other metal would also participate in the chelation between the nanoparticles and the bisphosphonated hyaluronic acid to generate the hydrogel. In some embodiments, the metal is selected from among bioactive metallic ions that promote tissue regeneration. Hydrogels can be loaded with multiple species of ions by incorporating multiple types of metal bisphosphonate nanoparticles. In this way, the hydrogels can produce and sustain the long-term continuous release of multiple types of metal ions simultaneously.

Although the methods described above include hyaluronic acid, it should be appreciated that the present invention is not limited to this monomer or biopolymer. The organic-inorganic hydrogels and the methods for their production can include one or more of any biopolymers. For example and without limitation, the hydrogels can include one or more of methacrylated or bisphosphonated derivatives of chitosan, cellulose, chondroitin sulfate, or gelatin. The degree of substitution, derivatization, or modification of the hyaluronic acid or other biopolymer can be within the range from 10% to 100%. The degree of substitution, derivatization, or modification can be within the range from 10% to 50%, from 20% to 60%, from 30% to 70%, from 40% to 80%, from 50% to 90%, or from 60% to 100%. The hyaluronic acid or other biopolymer can alternatively be modified with other reactive groups that contain unsaturated carbon-carbon bonds, such as acrylate, vinyl sulfone, and the like, that have been grafted onto the polymer chain.

IV. Methods of Filling Bone Defects

In some embodiments, the present invention provides several methods for filling bone defects. The methods include injecting into bone defects an organic-inorganic hybrid hydrogel as described above and herein, into bone defects, and seeding the organic-inorganic hybrid hydrogel with cells. The cells can be, for example and without limitation, any cells with osteogenic potential. These can include one or more of human mesenchymal stem cells (hMSCs), induced pluripotent stem cells (iPSCs), embryonic stem cells (ESCs), osteoblasts and osteoblast precursors such as MC3T3 cells, and others. In some embodiments, the cells include hMSCs.

The organic-inorganic hybrid hydrogel can include one or more biocompatible or bioactive cations. The biocompatible or bioactive cations can be, for example, alkaline earth metals. The alkaline earth metals can be, for example, one or more of magnesium, calcium, barium, or strontium. In some embodiments, the organic-inorganic hybrid hydrogel includes a plurality of methacrylated hyaluronic acid polymer chains, and a plurality of bisphosphonate-magnesium nanoparticles covalently linked to the plurality of methacrylated hyaluronic acid polymer chains.

The seeding of the organic-inorganic hybrid hydrogel with cells can occur prior to the injecting of the organic-inorganic hybrid hydrogel into bone defects. The seeding of the organic-inorganic hybrid hydrogel with cells can occur subsequent to the injecting of the organic-inorganic hybrid hydrogel into bone defects.

In some embodiments, the method further includes releasing bioactive ions from the implanted or injected organic-inorganic hybrid hydrogel into the bone defect. The bioactive ions can include, for example, one or more of magnesium, calcium, or strontium. The releasing can be at a particular concentration rate known to support tissue regeneration. The releasing can be sustained at or substantially near this concentration rate for a long-term period of, for example, 1 week, 2 weeks, 3 weeks, 4 weeks, 5 weeks, 6 weeks, 7 weeks, 8 weeks, 9 weeks, 10 weeks, 11 weeks, 12 weeks, or more than 12 weeks.

EXAMPLES

The present invention will be described in greater detail by way of specific examples. The following examples are offered for illustrative purposes only, and are not intended to limit the invention in any manner. Those of skill in the art will readily recognize that a variety of noncritical parameters can be changed or modified to yield essentially the same results.

All data are presented as mean+standard deviation. Statistical analysis was performed by using one-way ANOVA and Tukey's post hoc testing. Tests were conducted with a 95% confidence interval ($\alpha=0.05$).

Example 1. Synthesis of Methacrylated Hyaluronic Acid (HA)

Sodium hyaluronate was dissolved at 1 wt % in deionized water. Methacrylic anhydride was added dropwise with stirring at 4° C. The stirring mixture was maintained at pH 8-8.5 by continuously adding NaOH solution for approximately 8 hours. The mixture was dialyzed against NaCl solution and deionized water for 3 days, respectively, and then frozen at −80° C., lyophilized, and stored at −20° C. in powder form.

Example 2. Synthesis of Acrylated Bisphosphonate (Ac—BP)

N-acryloxysuccinimide and pamidronate disodium salt were dissolved together in NaOH solution (pH=8.0) and stirred for reaction. After 24 hours reaction at room temperature, the crude product was precipitated from water upon the addition of absolute ethanol. The precipitate was collected by centrifugation and washed with ethanol several times.

Example 3. Fabrication of MeHA-BP—Mg Hybrid Hydrogels

Methacrylated HA (MeHA) was synthesized by a simple esterification reaction, and the degree of substitution determined by $^1$H NMR to be approximately 100%. The simple mixing of MeHA, Ac—BP, and $MgCl_2$ solutions leads to the formation of the Ac—BP—Mg NP suspension in the MeHA solution within 5 minutes due to the rapid chelation between BP and $Mg^{2+}$. Subsequent UV-initiated polymerization of the free acrylate groups on the surface of the Ac—BP—Mg NPs and the methacrylate groups on the polymer chains produces the photo-crosslinked MeHA-BP—Mg hybrid hydrogels. The Ac—BP—Mg NPs are randomly crosslinked to each other or to the polymer chains and form micrometer sized micro-domains. These micro-domains formed by the clustering of the Ac—BP—Mg NPs act as the multivalent cross-linking domains to help stabilize the hydrogel network.

A schematic illustration of the fabrication of the MeHA-BP—Mg hybrid hydrogels is presented in FIG. 1. The transparent precursor solution containing MeHA, Ac—BP and $Mg^{2+}$ becomes opaque within 5 minutes after the initial mixing due to the in situ formation of the Ac—BP—Mg nanoparticles (FIG. 1, a and b). The MeHA-BP—Mg hybrid hydrogels are formed by UV irradiation for 10 minutes (FIG. 1, c). The self-assembly of the Ac—BP—Mg nanoparticle crosslinkers is then driven by the chelation of $Mg^{2+}$ and Ac—BP (FIG. 1, d). The MeHA-BP—Mg hybrid hydrogels are stabilized by the multivalent cross-linking micro-domains formed by the clustered Ac—BP—Mg nanoparticles (FIG. 1, e).

To further elucidate the function of these bead-like microdomains or microstructures, three control hydrogels were prepared, each having concentrations of selected components identical to those in the MeHA-BP—Mg hydrogels. The MeHA control hydrogel had the same concentration of MeHA only. The MeHA-BP control hydrogel had the same concentration of MeHA and Ac—BP without Mg. The MeHA&BP—Mg control hydrogel had the same concentration of MeHA, $MgCl_2$, and non-acrylated BP.

Example 4. Swelling Properties of the Hydrogels

Hydrogels often exhibit differential swelling behavior in response to the surrounding environment. This swelling behavior is critical to the hydrogels fitting into implantation areas. To test the swelling kinetics of the MeHA-BP—Mg hybrid hydrogels, cylindrical hydrogel samples (d=5 mm, h=2 mm) were prepared as in Example 3 and air dried to obtain the dry weights ($W_d$). The samples were then immersed in phosphate-buffered saline (PBS) buffer at pH 7.4, and the mass of each wet sample ($W_w$) was measured after different rehydration times. All measurements were done on triplicate samples (n=3). The swelling ratio (%) was calculated according to the formula:

$$\text{Swelling ratio}(\%) = \frac{W_w - W_d}{W_d} \times 100\%$$

Figure 2:
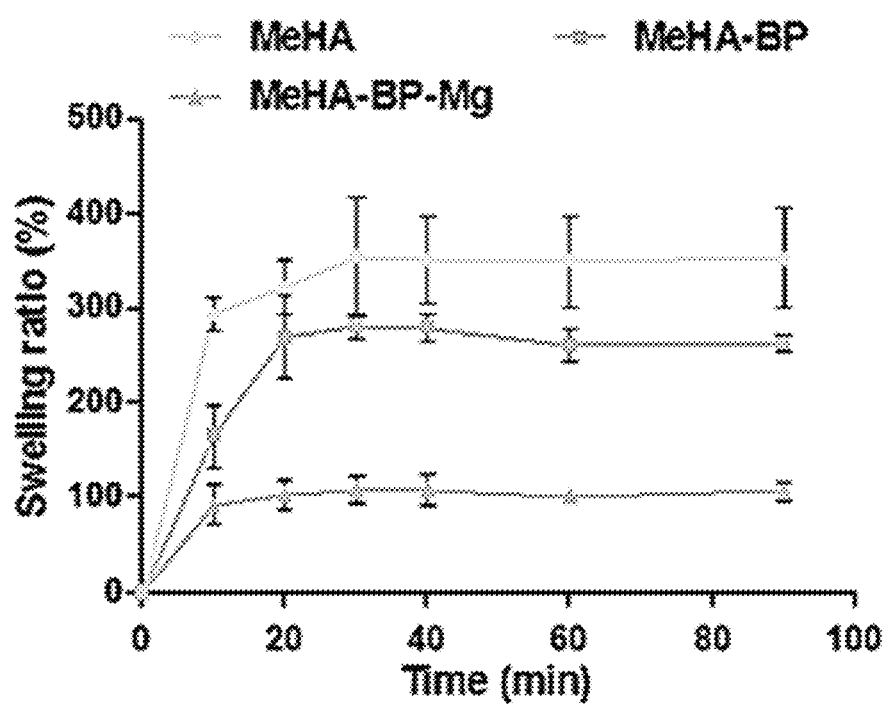
FIG. 2 is a graph of the swelling kinetics of hydrogels containing MeHA only ("MeHA"); or MeHA and Ac—BP ("MeHA-BP"); or MeHA, Ac—BP and $MgCl_2$ ("MeHA-BP—Mg") in buffer solution (pH 7.4).
Figure 3:
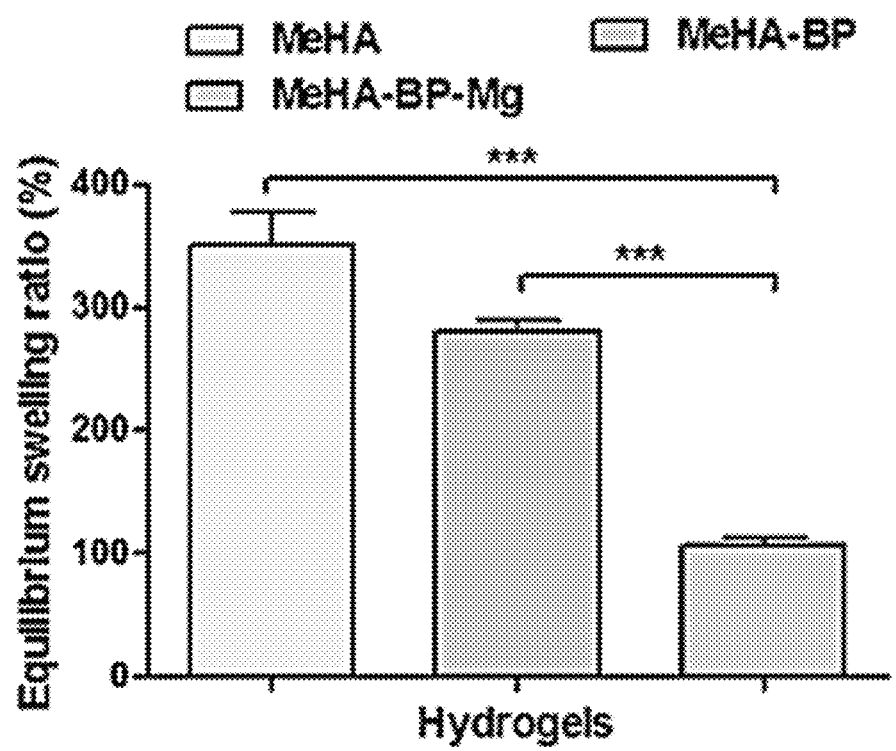
FIG. 3 is a graph of the equilibrium swelling ratios of the hydrogels of FIG. 2 (n=3); ***p<0.001.

The reswelling kinetics of the dried gels were studied over 2-hour periods. All hydrogels were found to swell quickly for the first 30 minutes, with a swelling plateau at an equilibrium level afterwards (FIG. 2). The photo-cross-linked pure MeHA hydrogels show the highest equilibrium swelling ratio, and the reswollen wet weight is more than 3 times the dry weight (FIG. 3). The addition of Ac—BP as the co-monomer leads to the increased crosslinking density and a slight reduction in the equilibrium swelling ratio of the MeHA-BP hydrogels (FIG. 3). Interestingly, the equilibrium swelling ratio of the MeHA-BP—Mg hybrid hydrogels is significantly lower than that of the MeHA and MeHA-BP hydrogels (FIG. 3). It is known that the equilibrium swelling ratio is dictated by the balance between the osmotic driving force to rehydrate the hydrophilic polymer chains and the entropy penalty involved in the polymer chain stretching during water absorption, and thus, the different swelling ratio may be due to the different microstructure of the hydrogels.

Example 5. Microscopic and Spectroscopy Analyses

To investigate the inner microstructures of the hybrid hydrogels, lyophilized hydrogel samples were mounted onto copper studs and sputter-coated with gold/palladium for 60 seconds. Then, scanning electron microscopy (SEM) images were acquired by using a field emission scanning electron microscope (Hitachi SU8010) with an iXRF energy-dispersive X-ray spectroscopy (EDS) system.

SEM images of the cross-sectional interior structure of the hydrogels (FIG. 4, a) show that the MeHA and MeHA-BP hydrogels of Example 3 are characterized by highly porous honeycomb-like structures visible at low magnification and relatively smooth pore surfaces at high magnification. In contrast, the hydrogels incorporated with $Mg^{2+}$ (MeHA-BP—Mg, MeHA&BP—Mg) exhibit densified structures attached with many nano/microbeads of various shapes and sizes. In the zoomed-in image of the MeHA&BP—Mg sample (FIG. 4, a), most beads are around 100-400 nm in diameter, which is similar to the size of the BP—Mg NPs or the physical aggregates of the NPs. However, in the MeHA-BP—Mg hydrogels, the beads are irregular in shape and much larger in size (approximately 2 µm in diameter). Without being bound by a particular theory, this implies that the Ac—BP—Mg NPs are clustered together due to the radical polymerization of the free acrylate groups on the NP surface and methacrylate groups on the polymer chains during the UV irradiation, thereby leading to the formation of the large sized bead-like micro-domains or microstructures in the MeHA-BP—Mg hydrogels. In contrast, in the MeHA&BP—Mg hydrogels, the BP—Mg NPs may not be capable of clustering via crosslinking due to the absence of the acrylate groups.

Figure 4A:
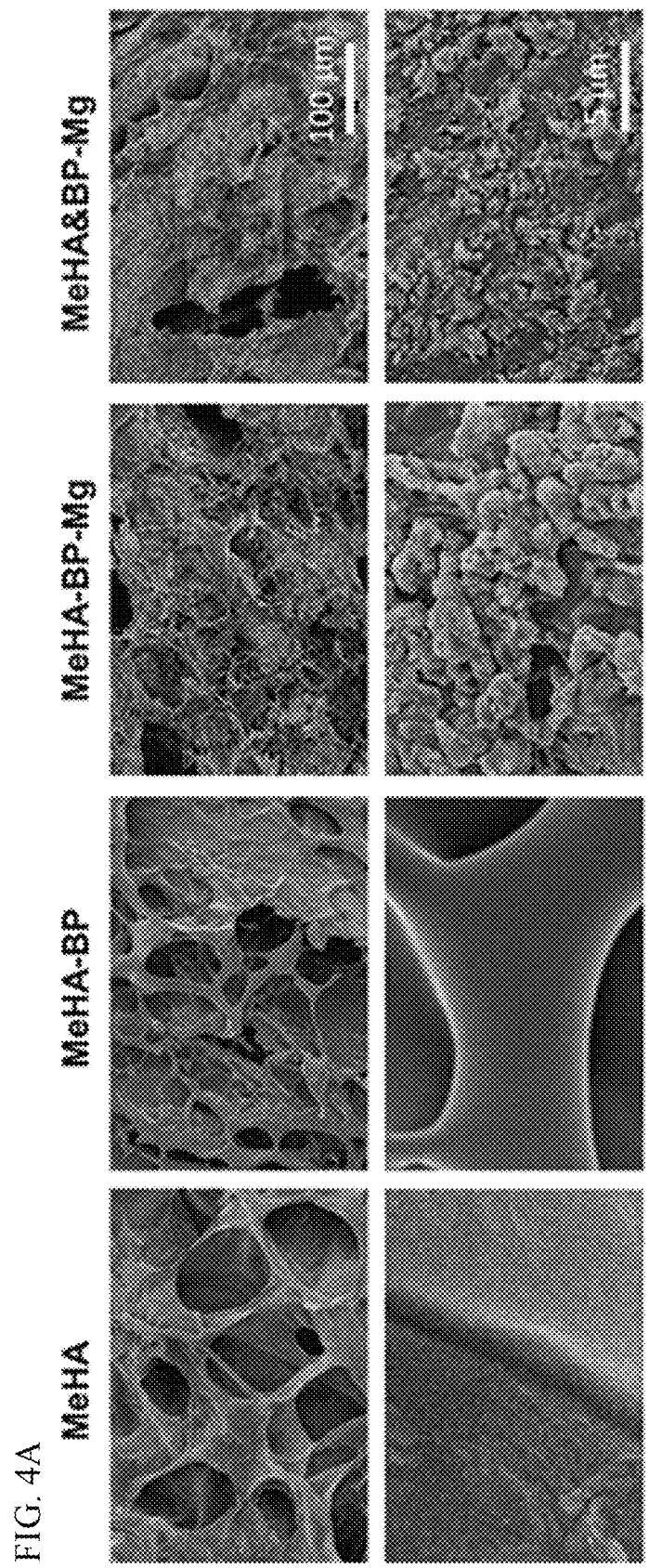
FIGS. 4A-4B presents results from scanning electron microscopy (SEM, FIG. 4A) and energy-dispersive X-ray spectroscopy (EDS, FIG. 4B) of hydrogels containing MeHA only ("MeHA"); or MeHA and Ac—BP ("MeHA-BP"); or MeHA, Ac—BP and $MgCl_2$ ("MeHA-BP—Mg"); or MeHA, BP, and $MgCl_2$ ("MeHA&BP—Mg").
Figure 4B:
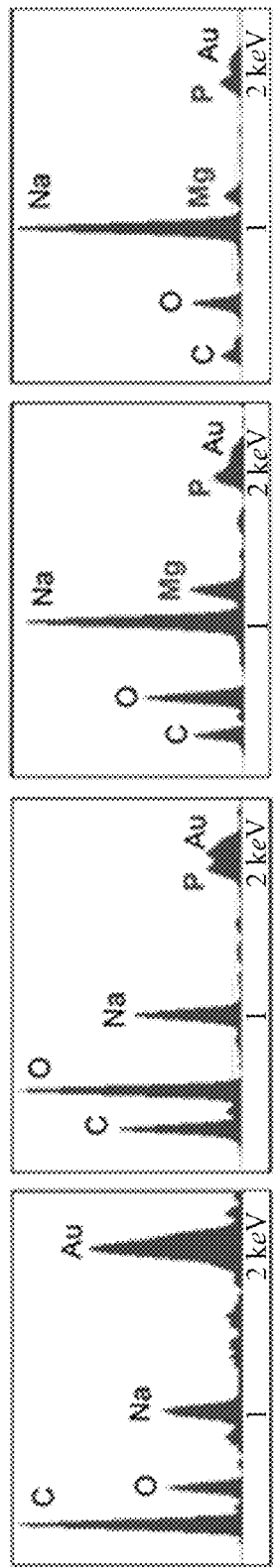

For the EDS analysis, in order to avoid the interference of elements in PBS, the hydrogel samples were prepared with deionized water, rinsed to remove un-crosslinked components, and then lyophilized. EDS analysis confirmed the substantial presence of phosphorus and magnesium in the bead-like microstructures in the hydrogels (FIG. 4, b). These substantial signals of the phosphorus and magnesium are only detected at the locations of the nano/microbeads observed in the SEM images, thereby verifying the involvement of the BP and $Mg^{2+}$ in the formation of these structures.

Example 6. Mechanical Properties of the Hydrogels

The mechanical properties of the MeHA-BP—Mg hybrid hydrogels were investigated by a uniaxial compression test. Compression tests of the hydrogels were performed with a Mach-1 Micromechanical System. Cylindrical hydrogel samples (d=5 mm, h=2 mm) were prepared in advance and equilibrated in PBS buffer. The compressive strain rate was set at 0.04 mm/min, and samples were compressed to failure. All tests were done on triplicate samples (n=3).

Figure 5:
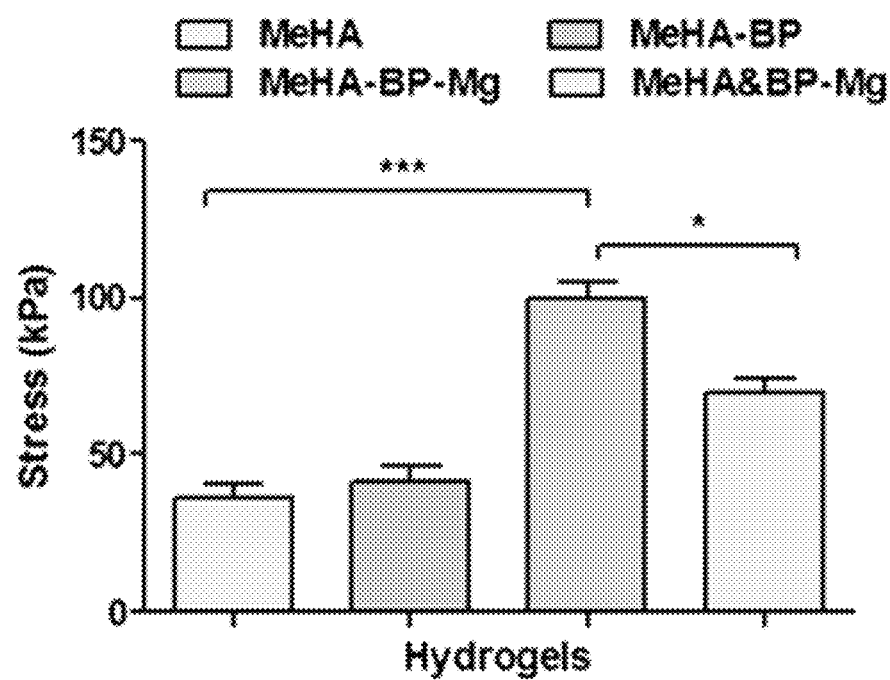
FIG. 5 is a graph of the average fracture stress of hydrogels containing MeHA only ("MeHA"); or MeHA and Ac—BP ("MeHA-BP"); or MeHA, Ac—BP and $MgCl_2$ ("MeHA-BP—Mg"); or MeHA, BP, and $MgCl_2$ ("MeHA&BP—Mg"); *p<0.05, ***p<0.001.

Results shown in FIG. 5 indicate that the photo-cross-linked pure MeHA hydrogels are brittle and rupture at low compressive strain (approximately 49.8%) with an average failure stress of 36.5 kPa. Although the addition of Ac—BP may influence the crosslinking density of hydrogels, the similar fracture stress of the MeHA-BP hydrogels as that of the MeHA hydrogels indicates that the addition of Ac—BP does not significantly affect the hydrogel stiffness in this case. In contrast, the hydrogels containing $Mg^{2+}$ (MeHA-BP—Mg, MeHA&BP—Mg) demonstrate a significantly higher fracture compressive stress. MeHA&BP—Mg hydrogels break at a stress of 69.4 kPa, and the MeHA-BP—Mg hydrogels break at an even higher stress (100.1 kPa), which is about 3 times of that of the MeHA hydrogels. It should be noticed that despite the similar chemical composition of the MeHA-BP—Mg and MeHA&BP—Mg hydrogels, the fracture stress of the former is 60.1% larger than that of the latter. Without being bound by a particular theory, this may be attributed to the multivalent crosslinking domains formed by the Ac—BP—Mg nanoparticles and MeHA, which may help absorb and dissipate loading energy.

Figure 6:
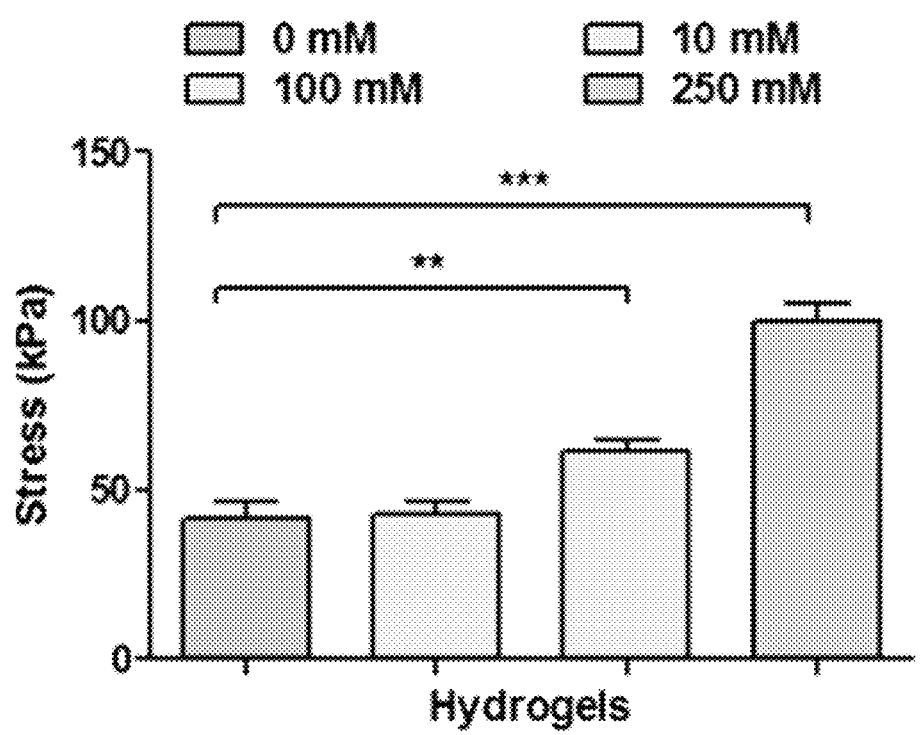
FIG. 6 is a graph of the average fracture stress of hydrogels containing MeHA, Ac—BP, and varying amount of $MgCl_2$ (0, 10, 100 or 250 mM) (n=3); p<0.01, *p<0.001.

The compression study also shows that the concentration of $Mg^{2+}$ is a critical parameter for the mechanical properties of the MeHA-BP—Mg hybrid hydrogels (FIG. 6). Decreasing the $Mg^{2+}$ concentration leads to the decreased fracture stress of the hydrogels, indicating a reduced number of the stabilizing crosslinking micro-domains due to the less Ac—BP—Mg NPs available at low $Mg^{2+}$ concentrations.

Example 7. Sustained Release of Magnesium from the Hydrogels

Although magnesium ion has been previously reported to promote bone regeneration, the burst and excessive release of $Mg^{2+}$ may actually lead to bone loss. Therefore, the release rate of $Mg^{2+}$ from the delivery vehicles should be carefully controlled. To study the influence of chemical immobilization and the presence of competitive ions on the release rate of $Mg^{2+}$ from the MeHA-BP—Mg hybrid hydrogels, the hydrogel samples were incubated in 1 mL of $Ca^{2+}/Mg^{2+}$-free PBS buffer or $CaCl_2$ solution (10 mM, 100 mM) at 37° C. At each preset time point, 100 μL of supernatant was collected, followed by the addition of 100 μL of fresh buffer or solution. All samples were in triplicate (n=3). The supernatant samples were analyzed by a magnesium colorimetric assay kit.

Figure 7:
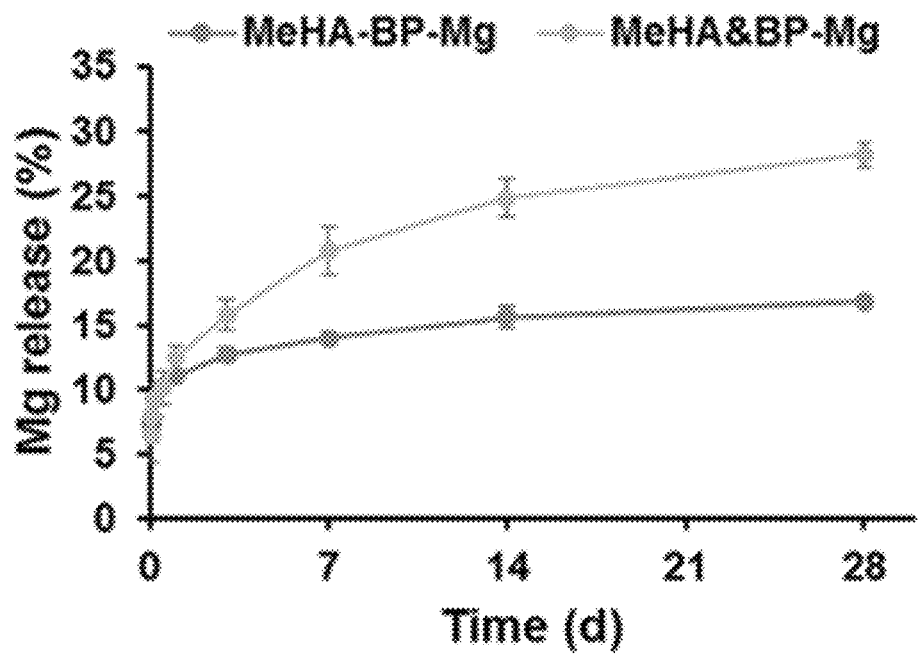
FIG. 7 is a graph of the cumulative release $Mg^{2+}$ from MeHA-BP—Mg and MeHA&BP—Mg hydrogels in PBS buffer (free of both $Ca^{2+}$ and $Mg^{2+}$).
Figure 8:
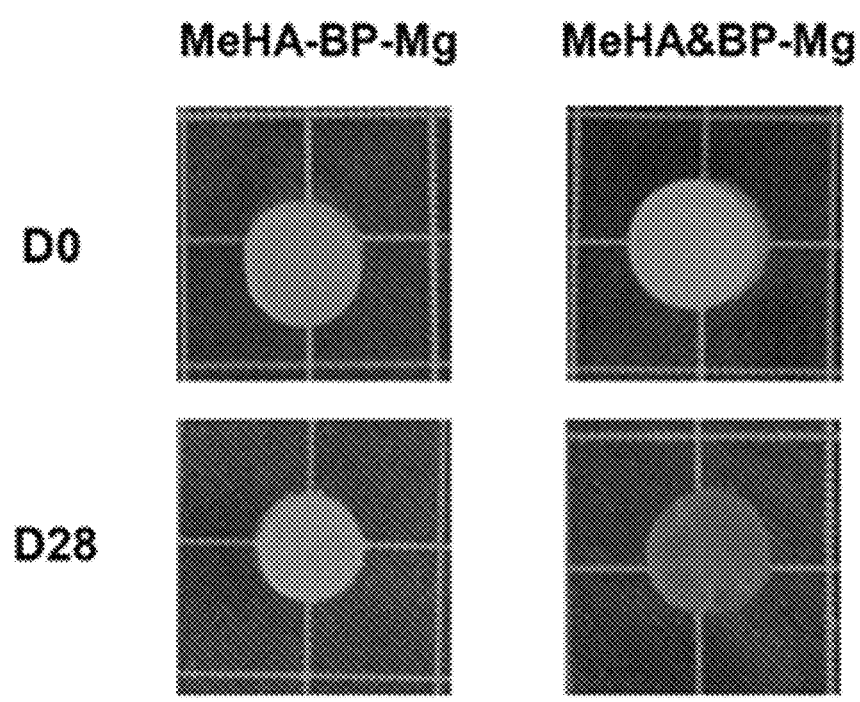
FIG. 8 presents photographs of the hydrogels before and after 28 days of incubation in a releasing buffer.

Results of the investigation of the release kinetics of $Mg^{2+}$ from the hybrid hydrogels incubated in PBS are presented in FIG. 7. Compared with the MeHA&BP—Mg hydrogels in which the BP—Mg nanoparticles are physically entraped, the MeHA-BP—Mg hybrid hydrogles exhibit significantly smaller initial burst release and slower subsequent release of $Mg^{2+}$. FIG. 8 shows photographs of the hydrogels before and after the 28 days of incubation in PBS. There is no obvious change in the opacity of the MeHA-BP—Mg hydrogels after the incubation, while the MeHA&BP—Mg hydrogels become translucent, indicating more loss of the BP—Mg NPs. Without being bound by a particular theory, the micro-domains formed by the polymerization induced clustering of the multivalent Ac—BP—Mg NPs in the MeHA-BP—Mg hydrogels may help to immobilize the Ac—BP—Mg NPs in the hydrogel network and slow down the release of $Mg^{2+}$ and loss of the NPs from the hydrogels. In contrast, the faster release of $Mg^{2+}$ and loss of the non-reactive BP—Mg NPs from the MeHA&BP—Mg hydrogels may be due to the lack of such stabilizing mechanisms found in the MeHA-BP—Mg hydrogels.

Example 8. Mineralization of Hydrogels In Vitro

During the bone remodeling process, the acidified microenvironment prompted by osteoclasts can promote the bone demineralization and increase the local concentration of $Ca^{2+}$, and both of the $H^+$ and $Ca^{2+}$ can facilitate the release of $Mg^{2+}$. Calcium phosphonates are known to be more stable and insoluble than the magnesium phosphonates. Therefore, the presence of calcium ions is expected to expedite the release of $Mg^{2+}$ from the MeHA-BP—Mg hydrogels by the competitive binding to the BP groups, thereby leading to calcification of the hydrogels.

To test mineralization in vitro, hydrogel samples were incubated in 1 mL of $CaCl_2$ solution (10 mM, 100 mM) at 37° C. At each preset time point, the mineralized hydrogel samples were collected and rinsed with deionized water for several times to remove loosely attached minerals. Each sample was then crushed and incubated in 100 μL of 1 M HCl overnight, followed by neutralization via the addition of 5 M NaOH. The calcium content of each sample was measured by a calcium colorimetric assay kit. All samples were in triplicate (n=3).

Figure 9:
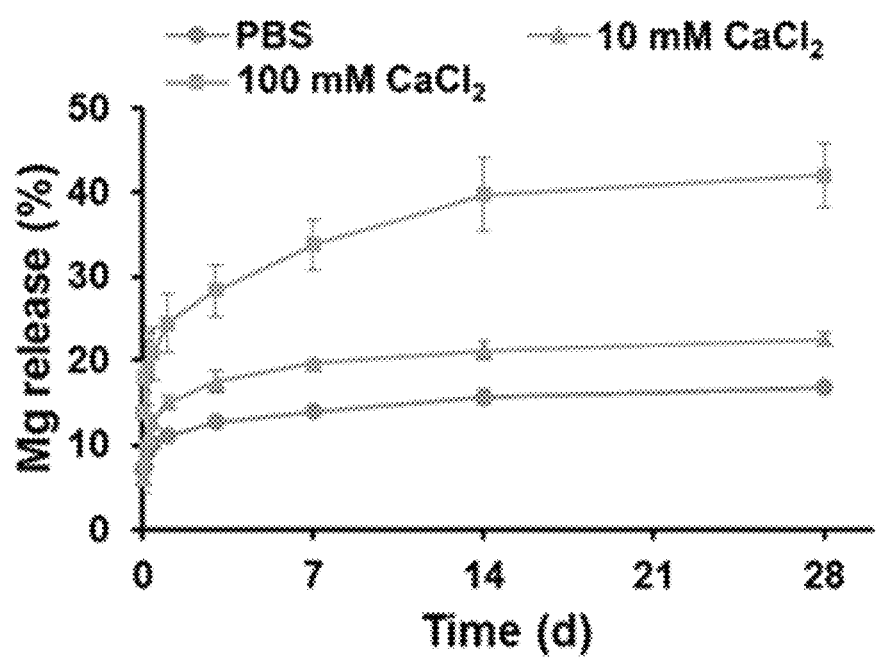
FIG. 9 is a graph of the cumulative release of $Mg^{2+}$ from MeHA-BP—Mg hydrogels incubated in PBS buffer (free of both $Ca^{2+}$ and $Mg^{2+}$) and $CaCl_2$ solutions.
Figure 10:
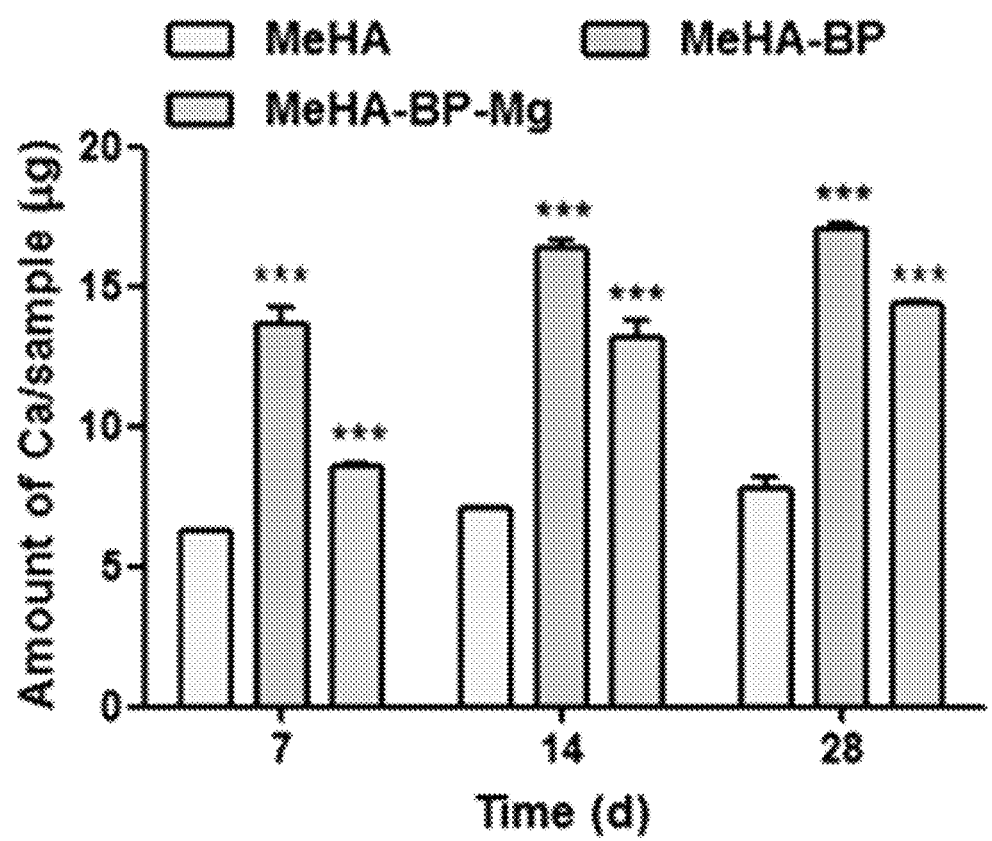
FIG. 10 is a graph of the amounts of calcium in the hydrogels after incubation in the calcification medium (100 mM $CaCl_2$) for different periods of time (7, 14 and 28 days) (n=3); ***p<0.001.

As shown in FIG. 9, the release rate of $Mg^{2+}$ from the MeHA-BP—Mg hybrid hydrogels demonstrates a dose-dependent increase as the incubation concentration of $Ca^{2+}$ increases. As for hydrogel calcification, although $Ca^{2+}$ can bind to the carboxylate groups of the HA, the binding affinity between $Ca^{2+}$ and BP groups is much higher. Hence, the amount of calcium deposited in the BP-containing hydrogels ("MeHA-BP", "MeHA-BP—Mg") is much more than that in the pure MeHA hydrogels ("MeHA") (FIG. 10). This finding demonstrates the potential of the MeHA-BP—Mg hydrogels in fostering calcification, which may facilitate the subsequent development of the mineralized bone matrix.

Example 9. Enhanced Adhesion and Osteogenesis of hMSCs

Besides promoting cell proliferation, $Mg^{2+}$ also efficiently enhances the attachment of osteoblasts to substrates in vitro. Human mesenchymal stem cells (hMSCs) were expanded to passage 4 and then seeded on two-dimensional (2D) MeHA-BP—Mg hydrogel substrates (d=15.6 mm, h=0.5 mm) to investigate cell adhesion and spreading. Cells were cultured in growth medium containing Minimum Essential Medium Eagle with Alpha Modifications (α-MEM) with 16.7% fetal bovine serum (FBS), 1% glutamine and 1% penicillin/streptomycin. After 1 or 3 days of culture, cells were fixed with 4% paraformaldehyde solution for 20 minutes at room temperature. The cytoskeletons were then stained with fluorescein phalloidin (FITC-phalloidin) fluorescent dye, and cell nuclei were stained with 4',6-diamidino-2-phenylindole (DAPI). Fluorescent images were acquired with a Nikon Ti-E Motorized Inverted Fluorescence Microscope.

Figure 11:
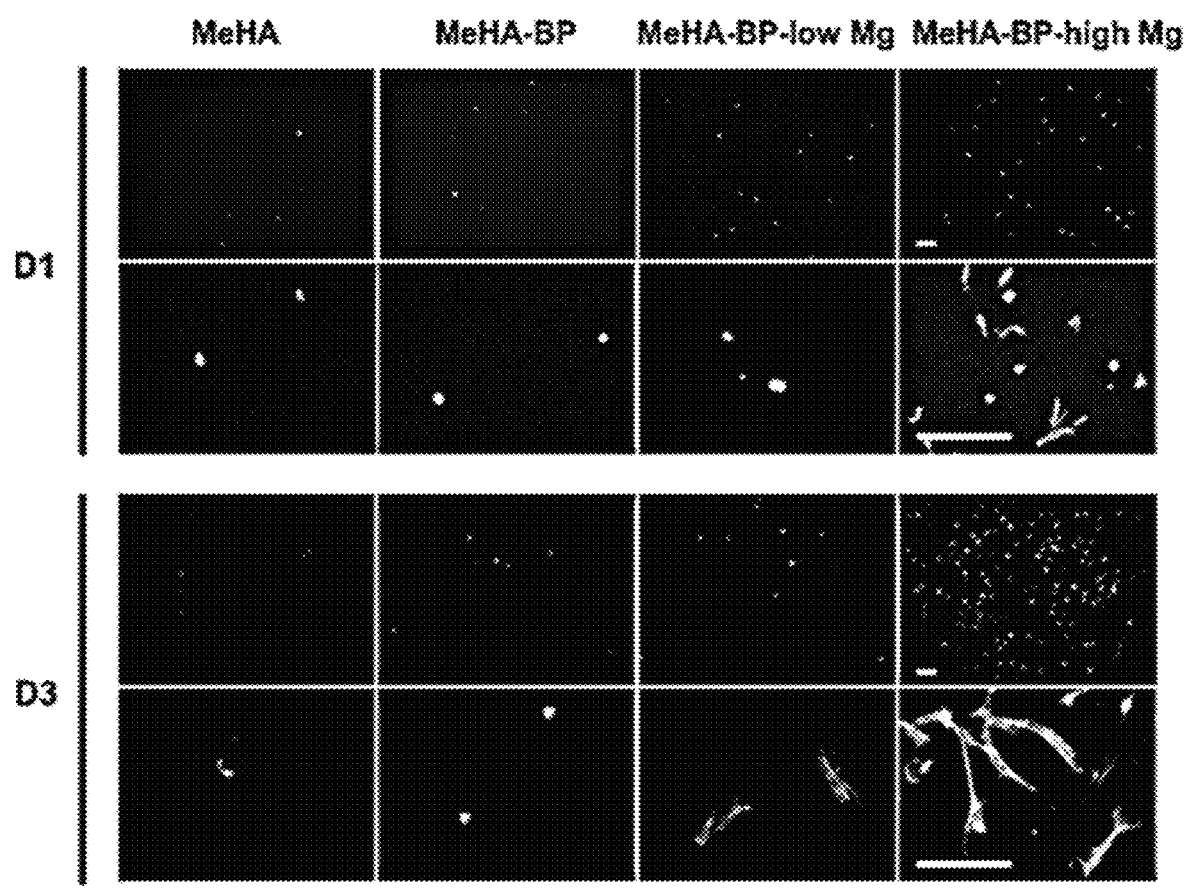
FIG. 11 presents images showing fluorescent staining against f-actin and nuclei in hMSCs after 1 or 3 days of culture in growth media; scale bar=200 µm. Hydrogels contain MeHA only ("MeHA"); or MeHA and Ac—BP ("MeHA-BP"); or MeHA, Ac—BP and $MgCl_2$ (100 mM) ("MeHA-BP-high Mg").
Figure 12:
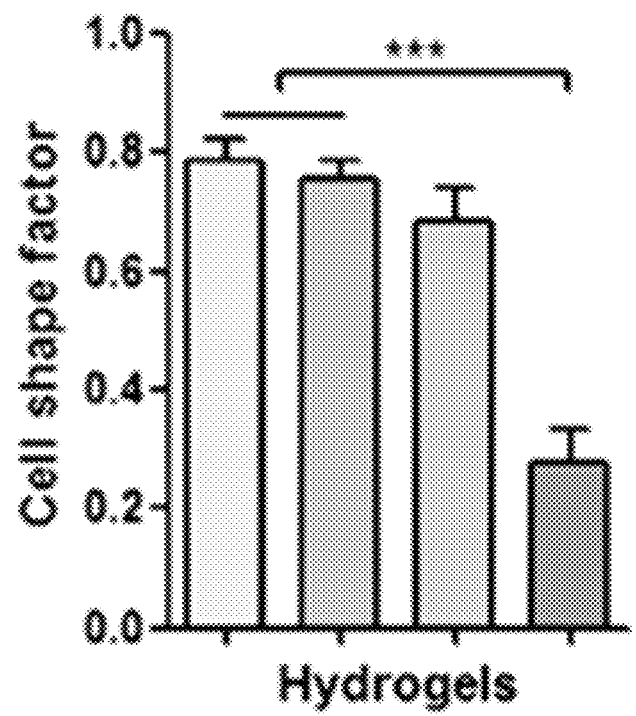
FIG. 12 is a graph of average cell shape factors of hMSCs on the MeHA (leftmost), MeHA-BP (middle left), MeHA-BP-low Mg (middle right) and MeHA-BP-high Mg (rightmost) hydrogels of FIG. 11 after 1 day of culture (n=3); ***p<0.001.
Figure 13:
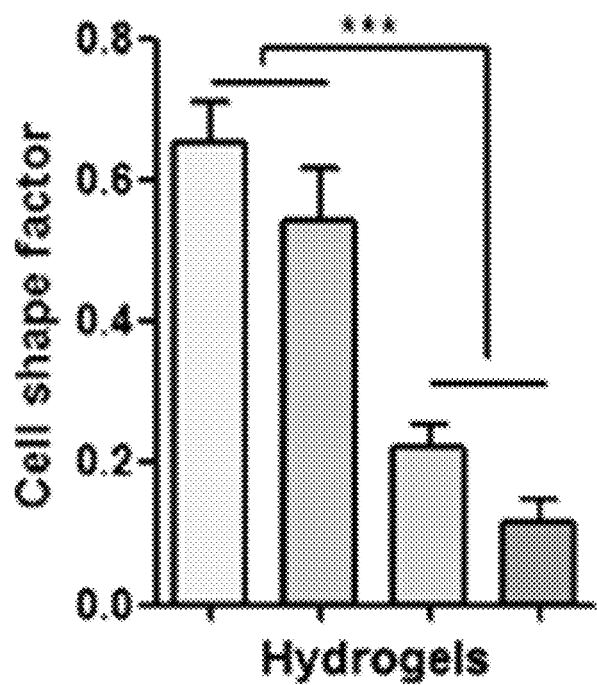
FIG. 13 is a graph of average cell shape factors of hMSCs on the MeHA (leftmost), MeHA-BP (middle left), MeHA-BP-low Mg (middle right) and MeHA-BP-high Mg (rightmost) hydrogels of FIG. 11 after 3 days of culture (n=3); ***p<0.001.

As is shown in FIG. 11, after 1 day of culture in growth media, very few hMSCs adhere to the surface of the MeHA and MeHA-BP hydrogels, and these cells show a round morphology with shape factor ($F=4\pi AP^{-2}$, where A is the area occupied by cell and P is the perimeter of cell) over 0.7 (FIG. 12). In contrast, with the increasing $Mg^{2+}$ concentration in the substrate hydrogels, significantly more cell adhesion and spreading is observed on the surface of the MeHA-BP—Mg hydrogels (FIG. 11). After 3 days, the adherent cells on the MeHA and MeHA-BP hydrogels still maintain a spherical morphology without obvious spreading, whereas the cells on the MeHA-BP—Mg hydrogels ("MeHA-BP-low Mg", "MeHA-BP-high Mg") spread extensively to adopt a typical spindle shape (FIG. 11) with the shape factors reaching 0.22 and 0.12, respectively (FIG. 13). Without being bound by a particular theory, this may be attributed to the interaction between $Mg^{2+}$ and the integrin receptors on the cell membrane. $Mg^{2+}$ displays high affinity to the ligand- and cation-binding A-domain (CD11bA) of integrins, and the $Mg^{2+}$ released from the hydrogel substrates may enhance the expression of integrins and facilitate the binding of physiological ligands to integrins. These bound ligands can further stabilize the active state of integrins and hence promote the cell-matrix adhesion.

Example 10. Osteogenic Differentiation of hMSCs

To assess the effect of $Mg^{2+}$ on the osteogenesis of hMSCs, 2D substrates with similar mechanical stiffness were prepared by adjusting MeHA concentration. RGD peptide was conjugated to all groups of the hydrogel substrates for further enhancement of the cell attachment, especially for the $Mg^{2+}$-free groups. Cells were cultured in an osteogenic medium (α-MEM, 16.67% FBS, 1% glutamine, 1% penicillin/streptomycin, 10 mM (3-glycerophosphate disodium, 50 mg/mL ascorbate, 0.1 mM dexamethasone), and the medium was changed 3 times per week. After osteogenic induction for 7 or 14 days, the seeded cells were fixed with 4% paraformaldehyde, rinsed in PBS several times, and permeabilized with 0.25% Triton X-100 in PBS for 30 minutes at room temperature. Human MSCs cultured on all hydrogel substrates spread extensively after 7 days of the osteogenic culture.

Figure 14:
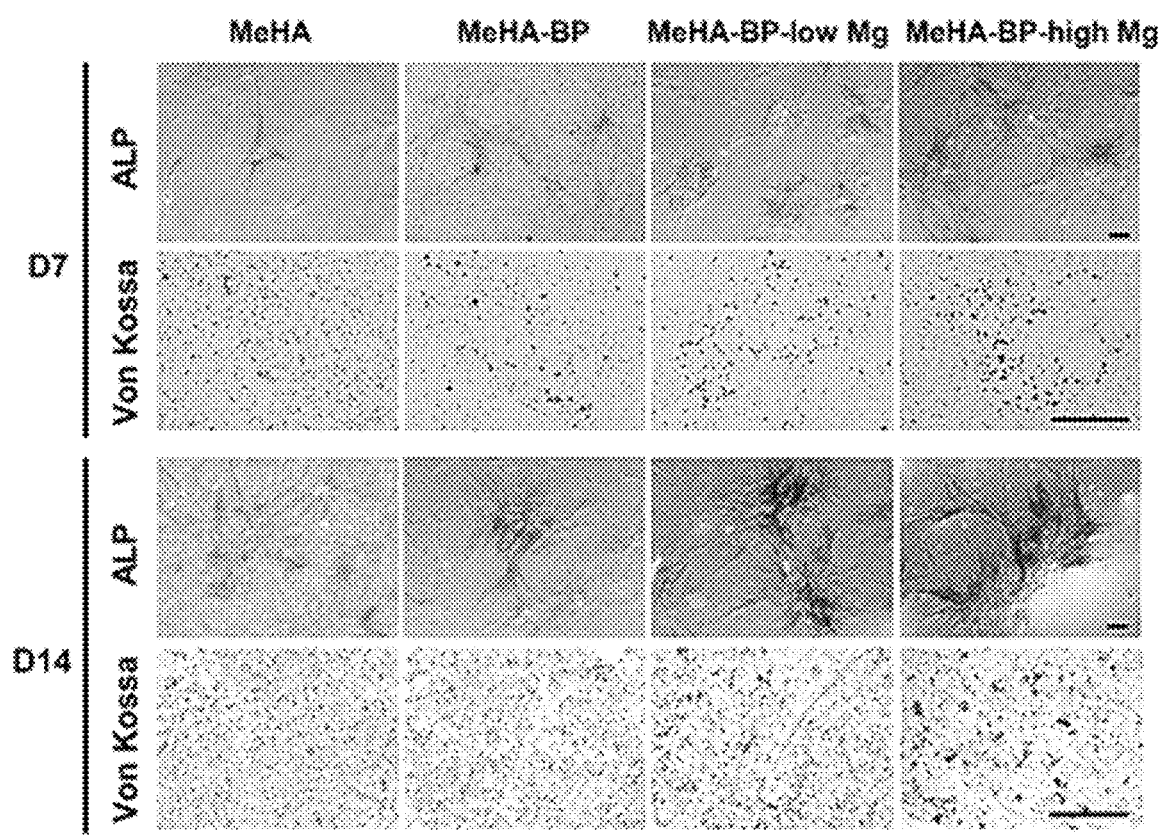
FIG. 14 presents images showing alkaline phosphatase and von Kossa staining of the hMSCs cultured on the 2D hydrogel substrates after 7 and 14 days of osteogenic differentiation; scale bar=100 µm. Hydrogels containing MeHA only ("MeHA"), or MeHA and Ac—BP ("MeHA-BP"), or MeHA, Ac—BP and $MgCl_2$ (10 mM) ("MeHA-BP-low Mg"), or MeHA, Ac—BP, and $MgCl_2$ (100 mM) ("MeHA-BP-high Mg").
Figure 15:
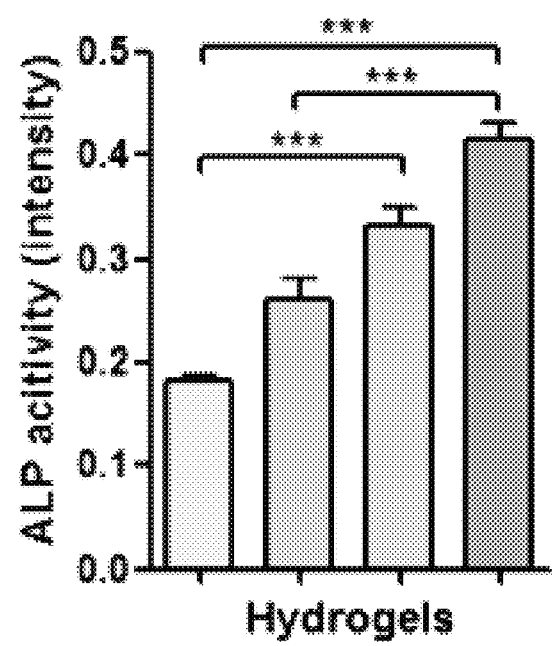
FIG. 15 is a graph of the average alkaline phosphatase activity of hMSCs on the MeHA (leftmost), MeHA-BP (middle left), MeHA-BP-low Mg (middle right) and MeHA-BP-high Mg (rightmost) hydrogels of FIG. 14 after 7 days (n=30); ***p<0.001.
Figure 16:
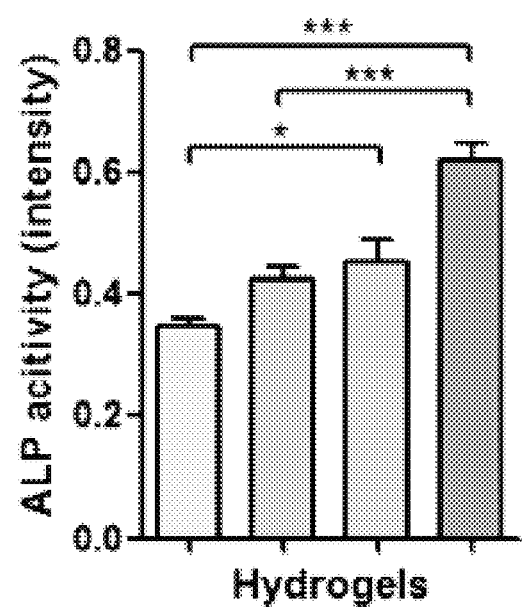
FIG. 16 is a graph of the average alkaline phosphatase activity of hMSCs on the MeHA (leftmost), MeHA-BP (middle left), MeHA-BP-low Mg (middle right) and MeHA-BP-high Mg (rightmost) hydrogels of FIG. 14 after 14 days (n=30); *p<0.05, ***p<0.001.

Staining against alkaline phosphatase (ALP), a key osteogenic marker, by Fast Blue staining after 7 and 14 days of the osteogenic induction shows significantly higher ALP activity in the hMSCs cultured on the MeHA-BP—Mg hydrogels ("MeHA-BP-low Mg", "MeHA-BP-high Mg") than that of the control groups ("MeHA", "MeHA-BP") (FIG. 14, FIG. 15, FIG. 16). Furthermore, the cells on the hydrogels containing higher $Mg^{2+}$ concentration show even higher ALP activity compared with those on the low magnesium hydrogels. Consistent with ALP result, the von Kossa staining to determine tissue calcification reveals more calcium deposition in the MeHA-BP—Mg groups than the control groups ("MeHA", "MeHA-BP") (FIG. 14). These findings show that the $Mg^{2+}$ released from the hydrogels may have contributed to the enhanced osteogenesis of the seeded hMSCs.

Example 11. Alternative Synthesis of HA-BP—Mg Hydrogels

Self-assembled HA-BP—Mg nanocomposite hydrogels can also be generated through an alternative route without chemical crosslinking (FIG. 17). In this scheme, HA is covalently grafted with BP groups, which promote the in situ formation of Ac—BP—Mg nanoparticles upon mixing with Mg ions and free Ac—BP (FIG. 17, a). These NPs function as multivalent crosslinker of HA chain to stabilize the obtained nanocomposite hydrogels. Furthermore, the in situ nucleation and growth of the NPs around the grafted BP leads to the "embedding" of the grafted BPs within the formed NPs (FIG. 17, b). This can significantly enhance the crosslinking strength between NPs and HA-BP macromers, thereby increasing the mechanical properties of the obtained hydrogels. In contrast, if the HA-BP macromers are mixed with the as-prepared Ac—BP—Mg NPs, weaker interactions are formed upon the coordination of the grafted BPs and the $Mg^{2+}$ at the surface of NPs, thereby yielding mechanically weaker hydrogels (FIG. 17, c). Furthermore, in this second generation HA-BP—Mg hydrogel synthesis, the non-embedded BPs (some grafted BPs and all free Ac—BPs) may loosely bind to the surface of NPs through dynamic and reversible coordination and contribute to the injectability and self-healing characteristics of the hydrogels. The acrylate groups at the surface of Ac—BP—Mg NPs can be further polymerized under UV irradiation, affording temporal and spatial control on the hydrogel stiffness via this secondary crosslinking (FIG. 17, d). Moreover, besides Mg ions, this strategy for the fabrication of self-assembled nanocomposite hydrogel also allows facile incorporation of other bioactive cationic species such as calcium ions and strontium ions. The obtain hydrogels can thus be capable of releasing multiple bioactive ions simultaneously for extended periods.

Figure 18B:
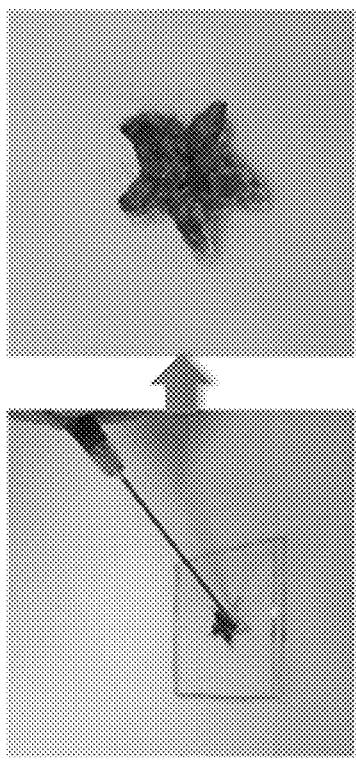
FIG. 18A-18C (FIG. 18A) Schematic illustration and a demonstration of the self-healing of the in situ HA-BP—Mg nanocomposite hydrogels.
Figure 18C:
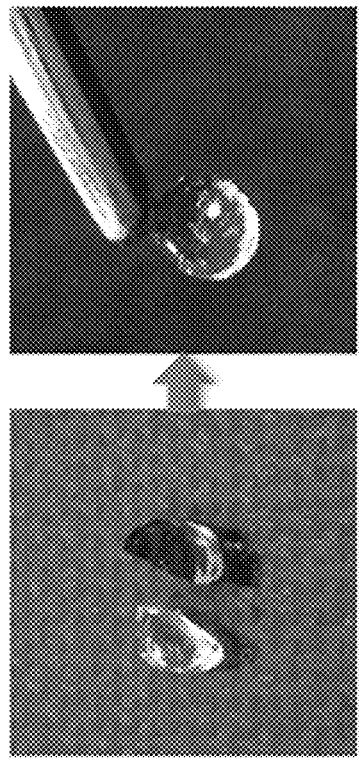
Figure 18A:
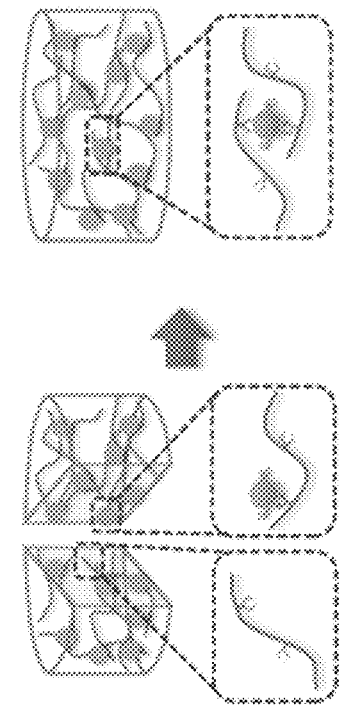

Example 12. HA-BP—Mg Nanocomposite Hydrogels are Self-Healing and Injectable The excellent self-healing property of the in situ HA-BP—Mg nanocomposite hydrogels was further demonstrated by the quick reintegration of cut pieces of hydrogels (half stained blue) into a new monolithic hydrogel within several minutes of juxtaposition (FIG. 18a). The subsequent compression tests show similar Young's moduli between the as-prepared and self-healed samples, and thereby indicating that the hydrogels can almost completely recover their mechanical properties after self-healing. Furthermore, the shear thinning behavior, excellent compressibility, and fast stress relaxation of the in situ hydrogels enables the facile injection and rapid remolding of the hydrogels to conform to the geometry of the injection sites. The in situ hydrogels can be injected through a G21 needle into molds of different shapes and quickly adapt to the shape of the mold (FIG. 18b). Moreover, this injection and remolding process shows little effect upon the encapsulated human mesenchymal stem cells (hMSCs), which remain largely viable following the injection and remolding of the hydrogels (FIG. 18c).

Figure 19A:
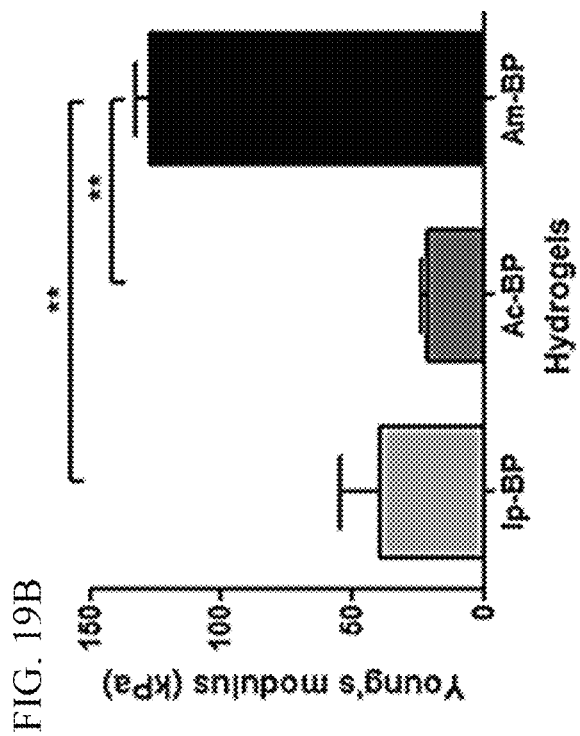
FIG. 19A-19B (FIG. 19a) Time sweep dynamic rheology study on HA-BP—Mg hydrogels containing different BP derivatives.
Figure 19B:
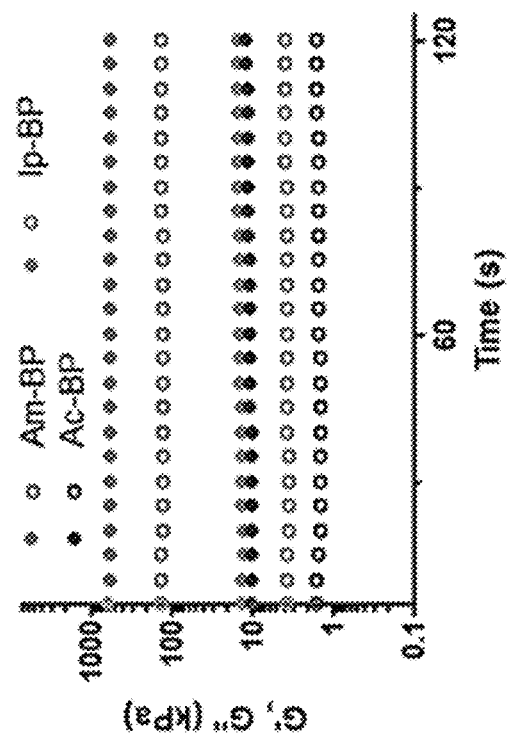

Example 13. HA-BP-Metal Hydrogels can be Formed by Bisphosphonate Derivatives with Additional Metal Ions Derivatives of bisphosphonate containing different tail groups can react with metal ions especially alkaline metal ions (such as $Ca^{2+}$ and $Mg^{2+}$) or transition metal ions (such as $Fe^{2+}$ and $Co^{2+}$) for the formation of the HA-BP-Metal (HA-BP—Mg as an example here) nanocomposite hydrogels (see Table 1, FIG. 19).

TABLE 1

Chemical structures of BP derivatives suitable for use in the present invention

| Name | Structure |
|---|---|
| Ac-BP | (acrylamide with $PO_3HNa$, OH, $PO_3HNa$ groups) |
| Am-BP | $H_2N$— with $PO_3HNa$, OH, $PO_3HNa$ |
| Ip-BP (imidazo-[1,2-a]-pyridinyl bisphosphonate.) | (imidazopyridinyl structure with $PO_3HNa$, OH, $PO_3HNa$) |

Figure 20A:
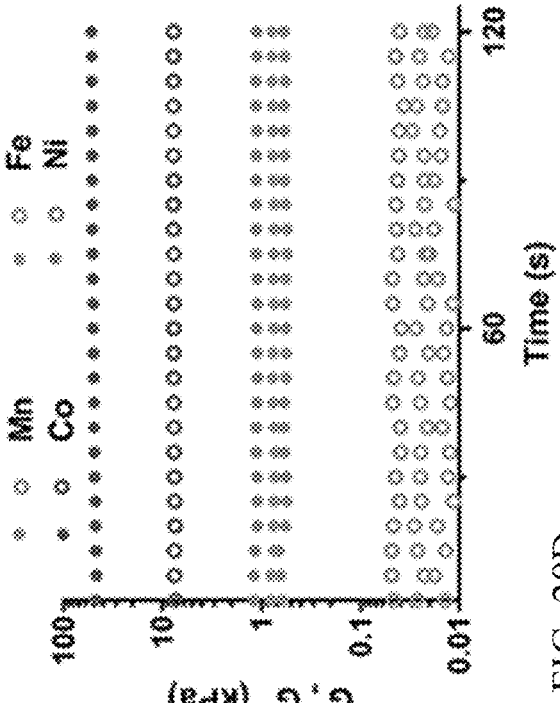
Figure 20B:
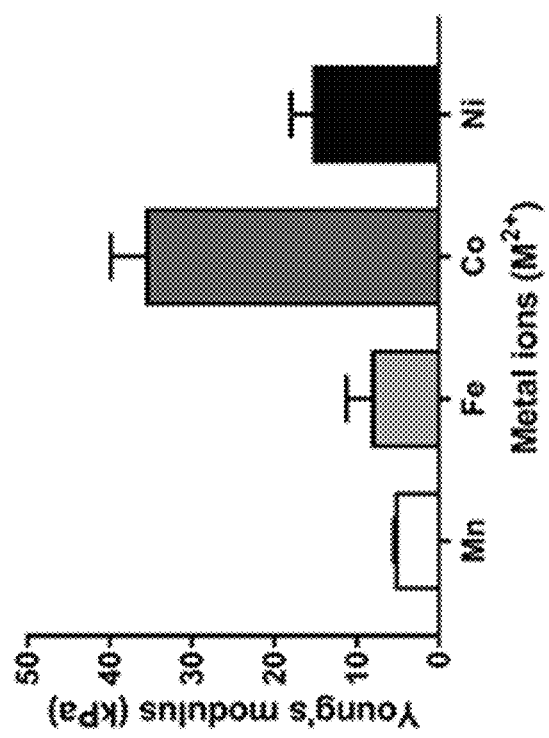
(FIG. 20b) Average Young's modulus of HA-BP—Mg hydrogels containing different BP derivatives.
Figure 20C:
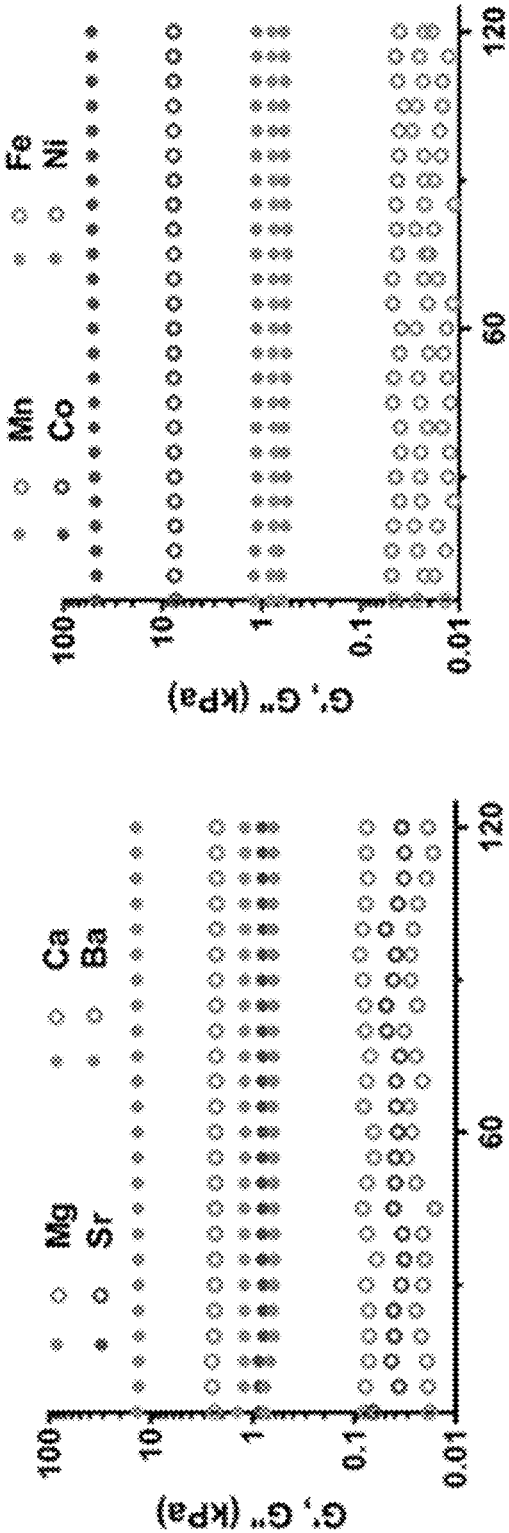
Figure 20D:
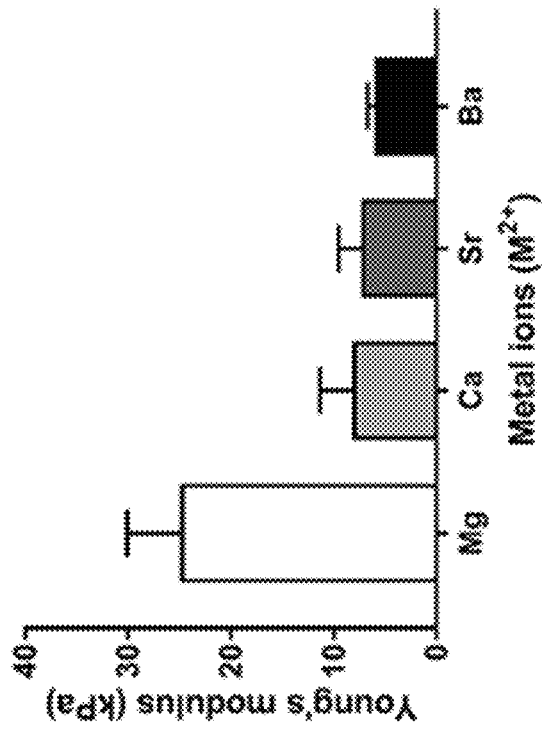

To further demonstrate the flexibility of gelation process with different metal ions, the HA-BP and Am—BP were dissolved in DI water, and the concentrated $MCl_2$ solution (M=Mg, Ca, Sr, Ba, Mn, Fe, Co, Ni) was add during vertex. The precursor solutions were successfully gelated by the divalent ions of the alkaline earth metals or the transition metal ions. The HA-BP—Mg hydrogels exhibit the highest storage modulus (G') and loss modulus (G"), and these moduli decreases in turn from $Ca^{2+}$ to $Ba^{2+}$, and this trend happens to be opposite to the size of the BP-M NPs. For the transition metal group, the HA-BP—Ni hydrogels show higher moduli than HA-BP—Mn and HA-BP—Fe ones. The HA-BP—Co hydrogels, holding the smallest NPs, indeed exhibited the highest values of the storage and loss moduli (FIG. 20b). Consistent with the trends of the rheological characterization, the Young's moduli of the hydrogels containing alkaline earth metal ions decrease form $Mg^{2+}$ to $Ba^{2+}$ (FIG. 20c), and the HA-BP—Co hydrogels still hold the highest Young's modulus among the hydrogels containing selective transition metal ions ($Mn^{2+}$, $Fe^{2+}$, $Co^{2+}$, $Ni^{2+}$) (FIG. 20d).

The fabrication of the alternative nanocomposite HA-BP-M ("M" for different metal ions) hydrogels containing different BP derivatives or metal ions should be similar to the original HA-BP—Mg hydrogels, which has been described in Example 11.

To synthesize the HA-BP macromer, the thiolglycolated bisphosphonate was conjugated to methacrylated HA (MeHA) macromers via the thiol-ene click reaction, and the HA-BP macromers were obtained after dialysis and lyophilization. Subsequently, the HA-BP and BP derivatives were dissolved in DI water, and the concentrated $MCl_2$ solution was add during vertex. The final concentrations of HA-BP, BP, and $MCl_2$ were 2 w/v %, 100 mM and 100 mM, respectively. The efficient coordination between BP and metal ions led to the efficient self-assembly of BP-M NP crosslinker, and thereby the ultrafast gelation within several seconds.

All references mentioned herein are incorporated by reference in the entirety to the same extent as if each reference was individually incorporated by reference. Where a conflict exists between the instant application and a reference provided herein, the instant application shall dominate.

What is claimed is:

1. A bisphosphonate-metal nanoparticle comprising an acrylated bisphosphonate chelated to an alkaline earth metal or transition metal.

2. An organic-inorganic hybrid hydrogel comprising:
a plurality of methacrylated polymer chains; and
a plurality of bisphosphonate-metal nanoparticles of claim 1 covalently linked to the plurality of methacrylated polymer chains.

3. The organic-inorganic hybrid hydrogel of claim 2, wherein at least a portion of the plurality of methacrylated polymer chains and at least a portion of the plurality of bisphosphonate-metal nanoparticles are arranged to form bead-like microstructures within the hydrogel, wherein each bead-like cross-linking domain has an average diameter within the range from 500 nm to 5 µm.

4. An injectable organic-inorganic hybrid hydrogel comprising:
a plurality of bisphosphonated polymer chains; and
a plurality of bisphosphonate-metal nanoparticles of claim 1 chelated to the plurality of bisphosphonated polymer chains.

5. The injectable organic-inorganic hybrid hydrogel of claim 4, wherein each nanoparticle has an average diameter within the range from 10 nm to 100 nm.

6. A method of filling a bone defect, the method comprising:
implanting or injecting an organic-inorganic hybrid hydrogel of claim 2 into the bone defect.

7. The method of claim 6, further comprising seeding the organic-inorganic hybrid hydrogel with live cells.

8. The method of claim 7, wherein the cells comprise human mesenchymal stem cells, induced pluripotent stem cells, embryonic stem cells, osteoblasts, or combinations thereof.

9. The method of claim 7, further comprising:
releasing alkaline earth metal or transition metal ions from the implanted or injected organic-inorganic hybrid hydrogel into the bone defect, wherein the release rate of the alkaline earth metal or transition metal ions supports tissue regeneration.

10. The method of claim 9, wherein the releasing is sustained for a period of at least 4 weeks.

11. The nanoparticle of claim 1, wherein the metal is Mg, Ca, Sr, Ba, Mn, Fe, Co, or Ni.

12. The hybrid hydrogel of claim 2, wherein the metal is Mg, Ca, Sr, Ba, Mn, Fe, Co, or Ni.

13. The hybrid hydrogel of claim 2, wherein the polymer is hyaluronic acid, chitosan, cellulose, chondroitin sulfate.

* * * * *